US007916832B2

(12) United States Patent
Hara et al.

(10) Patent No.: US 7,916,832 B2
(45) Date of Patent: Mar. 29, 2011

(54) RADIOGRAPHIC IMAGING APPARATUS

(75) Inventors: Hirotaka Hara, Hachioji (JP); Mamoru Umeki, Hachioji (JP); Hisashi Yonekawa, Hachioji (JP); Sumiya Nagatsuka, Hino (JP); Tomonori Gido, Kawasaki (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 374 days.

(21) Appl. No.: 12/089,697

(22) PCT Filed: Sep. 26, 2006

(86) PCT No.: PCT/JP2006/319005
§ 371 (c)(1),
(2), (4) Date: Apr. 9, 2008

(87) PCT Pub. No.: WO2007/043329
PCT Pub. Date: Apr. 19, 2007

(65) Prior Publication Data
US 2009/0272907 A1    Nov. 5, 2009

(30) Foreign Application Priority Data

Oct. 12, 2005  (JP) ................................. 2005-297431
Oct. 13, 2005  (JP) ................................. 2005-298613
Nov. 8, 2005   (JP) ................................. 2005-323477

(51) Int. Cl.
*A61B 6/00* (2006.01)
(52) U.S. Cl. ............... 378/20; 378/37; 378/62; 378/208

(58) Field of Classification Search .................... 378/20, 378/37, 62, 208
See application file for complete search history.

(56) References Cited

U.S. PATENT DOCUMENTS

| | | | | |
|---|---|---|---|---|
| 4,259,585 A * | 3/1981 | Novak et al. | | 378/37 |
| 5,930,328 A * | 7/1999 | Nakamura et al. | | 378/91 |
| 6,075,837 A * | 6/2000 | Roos et al. | | 378/98.2 |
| 7,344,306 B2 * | 3/2008 | Hsieh et al. | | 378/207 |
| 7,430,272 B2 * | 9/2008 | Jing et al. | | 378/37 |
| 7,443,950 B2 * | 10/2008 | Sendai | | 378/37 |
| 2003/0215061 A1 * | 11/2003 | Sakaida | | 378/210 |
| 2004/0109530 A1 * | 6/2004 | Amitani et al. | | 378/37 |
| 2004/0131145 A1 * | 7/2004 | Ohara | | 378/37 |
| 2007/0081625 A1 * | 4/2007 | Sendai | | 378/37 |

* cited by examiner

*Primary Examiner* — Edward J Glick
*Assistant Examiner* — Alexander H Taningco
(74) *Attorney, Agent, or Firm* — Finnegan, Henderson, Farabow, Garrett & Dunner, L.L.P.

(57) ABSTRACT

A control device of a breast image radiographing apparatus relating to the present invention controls a driving device, in response to a press-down of a position adjustment switch of an input device, so as to adjust the position of a subject table. The position of compression board is adjusted by the operator such as a radiographing technician, the subject H is pressed and fixed, and when the enlargement factor of the phase contrast radiographing is inputted through the input device, the control device controls a driving device according to the positions of the subject table and the compression board and the inputted enlargement factor, so as to make a holding member ascend and descend and thereby the relative distances of the subject table to a radiation source and to a radiation image detector are adjusted to distances satisfying the enlargement factor=(R1+R2)/R1.

11 Claims, 14 Drawing Sheets

FIG. 6

CASE OF R1+R2=1555

| ENLARGEMENT FACTOR (TIMES) | 1.75 | 1.46 |
|---|---|---|
| R1(mm) | 889 | 1065 |
| R2(mm) | 666 | 490 |
| R1+R2(mm) | 1555 | 1555 |
| OUTPUT (RADIATION DOSE PER UNIT TIME) | D (0.54) | D(0.37) |
| UNIFORMITY (HEAL EFFECT) | A | A |
| SHARPNESS | A | B |
| GRAININESS | A | A |
| SCATTERED RADIATION CONTENT RATE | A | A |
| PHASE CONTRAST EFFECT | A | A |
| OVERALL JUDGMENT | C | C |

CASE OF R1+R2=1140

| ENLARGEMENT FACTOR (TIMES) | 1.75 | 1.46 |
|---|---|---|
| R1(mm) | 650 | 780 |
| R2(mm) | 490 | 360 |
| R1+R2(mm) | 1140 | 1140 |
| OUTPUT (RADIATION DOSE PER UNIT TIME) | 1 | C(0.7) |
| UNIFORMITY (HEAL EFFECT) | B | A |
| SHARPNESS | A | B |
| GRAININESS | A | A |
| SCATTERED RADIATION CONTENT RATE | A | B |
| PHASE CONTRAST EFFECT | A | B |
| OVERALL JUDGMENT | A | B |

CASE OF R1+R2=950

| ENLARGEMENT FACTOR (TIMES) | 1.75 | 1.46 |
|---|---|---|
| R1(mm) | 543 | 650 |
| R2(mm) | 407 | 300 |
| R1+R2(mm) | 950 | 950 |
| OUTPUT (RADIATION DOSE PER UNIT TIME) | B(1.4) | B(1) |
| UNIFORMITY (HEAL EFFECT) | C | B |
| SHARPNESS | B | B |
| GRAININESS | A | A |
| SCATTERED RADIATION CONTENT RATE | B | C |
| PHASE CONTRAST EFFECT | B | C |
| OVERALL JUDGMENT | B | C |

CASE OF R1+R2=750

| ENLARGEMENT FACTOR (TIMES) | 1.75 | 1.46 |
|---|---|---|
| R1(mm) | 429 | 514 |
| R2(mm) | 321 | 236 |
| R1+R2(mm) | 750 | 750 |
| OUTPUT (RADIATION DOSE PER UNIT TIME) | A(2.3) | B(1.6) |
| UNIFORMITY (HEAL EFFECT) | D | C |
| SHARPNESS | B | B |
| GRAININESS | A | A |
| SCATTERED RADIATION CONTENT RATE | C | D |
| PHASE CONTRAST EFFECT | D | D |
| OVERALL JUDGMENT | D | D |

RADIOGRAPHIC IMAGING APPARATUS

TECHNICAL FIELD

The present invention relates to a radiographic imaging apparatus, and in particular, to a radiographic imaging apparatus capable of radiographing a phase contrast image.

BACKGROUND OF THE INVENTION

In general, a radiographic imaging apparatus that utilizes a function of radiation passing through substances is used widely for medical image diagnosis and for non-destructive examination. For the radiographic imaging apparatus used for mammography, in particular, there has been usually conducted a method to radiograph by fixing a subject on a subject table that is integrated with a radiation image detector. However, in this method, there have been problems that image contrast is not enhanced sufficiently and image sharpness is insufficient as a medical imaging apparatus used to make out microscopic structure of a specific region such as a pathological portion of a breast, although a subject can be radiographed on the exact size.

In recent years, therefore, there has been proposed a radiographic imaging apparatus that radiographs a phase contrast image. The phase contrast image is one which is also called a refraction contrast image, and is one which was earlier said to be obtained by radiographing with monochromatic parallel radiation obtained from radiation source such as SPring-8 or by radiographing with a micro-focus radiation source having a focus size of about 10 (μm). However, it has been found that the phase contrast image can be obtained even by a radiation source (small focus radiation source having focus size 30-300 (μm)) used in general medical facilities.

For example, in Patent Document 1, there is described a technology to obtain an effect of edge enhancement without using a synchrotron radiation light that requires a large-sized apparatus and without using a small-sized X-ray light source having an X-ray focus size that can be regarded as a point source of light. This Patent Document 1 shows that, when X-ray focus size D is 30 (μm) or more, distance R1 covering from an X-ray tube representing a radiation source to a subject represents an area satisfying an expression of $R1 \geq (D-7)/200$ (m), and when distance R2 is 0.15 (m) or more, an edge enhanced image can be obtained. In this case, the radiographing is enlarging one with an enlargement factor that is expressed by $(R1+R2)/R1$.

In the past, incidentally, when changing an enlargement factor in a radiographic imaging apparatus that conducts phase contrast radiographing, the aforesaid R1 is fixed and R2 is changed to change the enlargement factor as is shown in Patent Document 2, for example.

Patent Document 1: Unexamined Japanese Patent Application Publication No. 2001-91479

Patent Document 2: Unexamined Japanese Patent Application Publication No. 2004-173879

DISCLOSURE OF THE INVENTION

Problems to be Solved by the Invention

FIG. 7 shows schematically positional relationships for radiation source 6, subject H, detector holding section 12 (numerals in the figure shows an enlargement factor) that holds a radiation image detector (X-ray detector) and floor and ceiling in a radiographing chamber where phase contrast radiographing is conducted, in the case of radiographing a breast through phase contrast radiographing in a conventional radiographic imaging apparatus. Since distance R1 between radiation source 6 and subject H is fixed in the conventional radiographic imaging apparatus, the radiation source 6 is positioned to be higher than a position of subject H by the distance of R1 in the vertical direction. In other words, a position of the top of the radiation source 6 is made to be higher, depending on the position of a subject (a height from a floor to subject H, when the subject H is a breast). On the other hand, a space of the radiographing chamber is limited. Therefore, when a position of a breast representing subject H is high in the case of a patient such as a tall patient, and a distance between a position of subject H and a ceiling is less than R1, it is impossible to radiograph. Further, a position of detector holding section 12 is determined based on a position of subject H and an enlargement factor, and the greater the enlargement factor is, the greater R2 is. Therefore, if a position of a breast representing subject H is low, such as an occasion where a patient is short, there is sometimes an occasion where the enlargement factor which makes radiographing possible is restricted.

The purpose of the invention is to expand a range of subject positions which make phase contrast radiographing possible and thereby to broaden a range of patients in a radiographic imaging apparatus that conduct phase contrast radiographing.

Means to Solve the Problems

In one embodiment of the invention, the invention comprises a radiographic imaging apparatus having therein a radiation source having a focus size D of 30 (μm) or more, a detector holding device that holds a radiation image detector which detects a radiation emitted from the aforesaid radiation source and having passed through a subject, and a subject table for fixing a subject, arranged between the aforesaid radiation source and the aforesaid detector holding device. The radiographic imaging apparatus conducts phase contrast radiographing under the condition of $R1 \geq (D-7)/200$ (m) for distance R1 from the radiation source to the subject, wherein there are provided a holding device for keeping a distance between the radiation source and the detector holding device to be a constant distance and an adjusting device that adjusts a relative distance between the subject table and the radiation source and a relative distance between the subject table and the radiation image detector.

In one embodiment of the invention, the distance L (m) between the radiation source and the detector holding device is 0.95 (m) or more. In an embodiment of the invention, the focus size D is 100 (μm).

In one embodiment of the invention, the aforesaid subject table can be mounted after selecting from a plurality of different sizes, and a subject table size information obtaining device that obtains size information of the aforesaid mounted subject table and a control device to control the adjusting device based on the aforesaid obtained object table size information are provided.

In another embodiment of the invention, the aforesaid control device controls the aforesaid adjusting device so that the aforesaid relative distance is adjusted to the distance which causes radiation images of all subjects held by the subject table to be detected by the radiation image detector held by the detector holding device, based on the aforesaid obtained subject table size information.

In one embodiment, the invention further comprises a detector size obtaining device that obtains size information of the aforesaid radiation image detector, and the control means described above controls the adjusting device based on the aforesaid obtained subject table size information and on the aforesaid size information of the radiation image detector.

In another embodiment, the invention further comprises a setting device that sets an enlargement factor for radiographing, and there is provided a control device that judges whether the radiation image of the overall subject held on the subject table can be detected by a radiation image detector held on the aforesaid detector holding device or not, when radiographing at the aforesaid set enlargement factor for radiographing based on aforesaid obtained information of a subject table size and on the aforesaid set enlargement factor for radiographing and controls the aforesaid adjusting device based on the results of the judgment.

In other embodiments, the invention further comprises a warning device that gives a warning, and the aforesaid control device causes the warning device to give a warning when a part of a radiation image of a subject held on the subject table is judged to be unable to be detected by the aforesaid radiation image detector in the case of radiographing at the set enlargement factor for radiographing, and when a radiographing permission signal at the set radiographing enlargement factor is inputted, the control device controls the adjusting device to adjust the relative distance, based on the set radiographing enlargement factor.

In one embodiment of the invention, the control device judges whether the radiation image of the overall subject held on the subject table can be detected by the radiation image detector held on the detector holding device or not, based on the acquired size information for a subject table and on the acquired size information for the radiation image detector, when radiographing at the set enlargement factor is conducted.

In another embodiment of the invention, the detector holding device has an attaching-detaching slot through which the radiation image detector is attached or detached, then, a radiation shading member that covers a space between the subject table and the detector holding device is provided, and an opening through which the radiation image detector can pass is formed at the position of the radiation shading member corresponding to the attaching-detaching slot in the detector holding device.

In other embodiments of the invention, the radiation shading member is composed of the first radiation shading member that covers a space between the subject table and the detector holding device in the case of radiographing at the first enlargement factor for radiographing and of the second radiation shading member that covers a space formed between the first radiation shading member and the subject table in radiographing at the second enlargement factor for radiographing when a distance between the subject table and the detector holding device is relatively longer than at the first enlargement factor, and the aforesaid opening section is formed on the first radiation shading member.

EFFECT OF THE INVENTION

In one embodiment of the invention, a range of subject positions where phase contrast radiographing is possible is extended in the radiographic imaging apparatus that conducts phase contrast radiographing, thus it can be applied to more patients.

In further embodiments of the invention, it is possible to assure the phase contrast effects of radiographed images.

In other embodiments, it is possible to prevent a partial missing image of a subject caused in accordance with a subject table size to be used, because a relative distance between a subject table and a detector holding device is adjusted based on a subject table size.

In other embodiments, it is possible to prevent a partial missing image of a subject caused in accordance with a size of a subject table to be used and with a size of a radiation image detector, in a radiographic imaging apparatus wherein a size of a radiation image detector is variable.

In additional embodiments of the invention, it is possible to prevent a partial missing image of a subject caused in accordance with a subject table size to be used, when conducting radiographing at the set enlargement factor for radiographing.

In further embodiments, it is possible to prevent a partial missing image of a subject caused in accordance with a size of a subject table to be used and with a size of a radiation image detector, in a radiographic imaging apparatus wherein a size of a radiation image detector is variable.

In further embodiments of the invention, it is possible to improve easiness for attaching and detaching of a radiation image detector when using a radiation shading member, in the radiographic imaging apparatus that conducts phase contrast radiographing.

In additional embodiments of the invention, it is possible to conduct radiographing using a radiation shading member for any of the first and second enlargement factors for radiographing, and it is possible to attach and detach the radiation image detector easily while using the radiation shading member.

BRIEF DESCRIPTION OF THE DRAWINGS

FIG. 6 is a diagram showing results of evaluation for visibility of each radiographed image when conducting radiographing by changing distance L (R1+R2) between radiation source 6 and detector holding section 12 and by changing an enlargement factor in the breast image radiographing apparatus 1.

DESCRIPTION OF SYMBOLS

Figure 1:
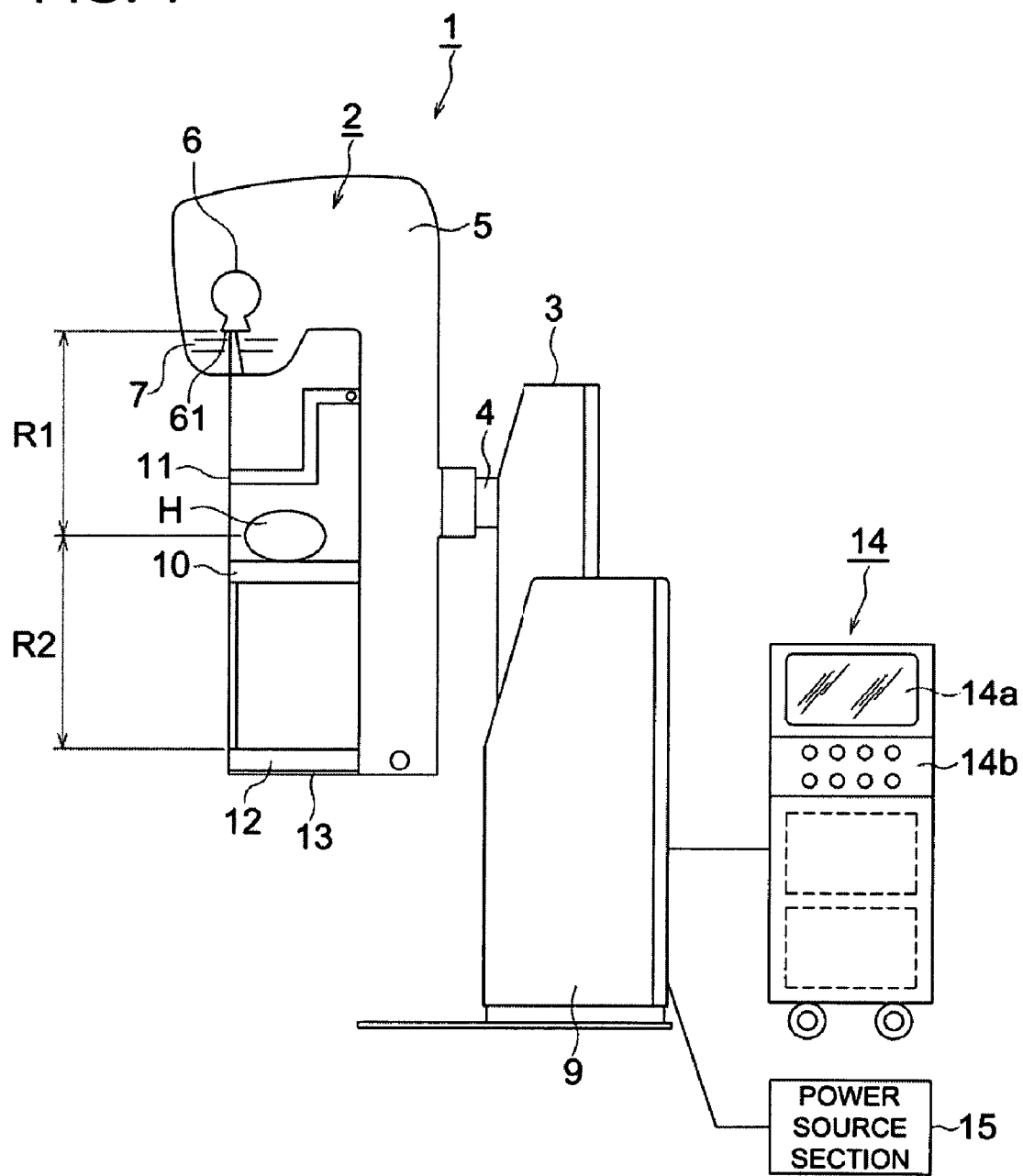
FIG. 1 is a diagram showing an example of a structure of breast image radiographing apparatus 1 relating to the invention.

1. Breast image radiographing apparatus
2. Radiographing apparatus main body section
3. Supporting base table
4. Supporting shaft
6. Radiation source
7. Aperture device
8. Holding member
9. Maim body section
10. Subject table
11. Compression board
12. Detector holding section
13. Radiation dose detector
14. Operation device
14a. Input device
14b. Display device
15. Power source section
16. Control device
17. Driving device
18. Position detecting section
19. Subject table detecting section
20. Driving device
21. Bus
22. First radiation shading member
22a, 22b. Screw hole
22c. Opening section
23. Second radiation shading member
23a, 23b. Magnet
23c. Engagement protrusion

PREFERRED EMBODIMENT FOR PRACTICING THE INVENTION

First Embodiment

Breast image radiographing apparatus 1 relating to the present embodiment is a radiographic imaging apparatus that conducts phase contrast radigraphing. The structure of the breast image radiographing apparatus 1 in First Embodiment will be described as follows, referring to the drawings.

Figure 2:
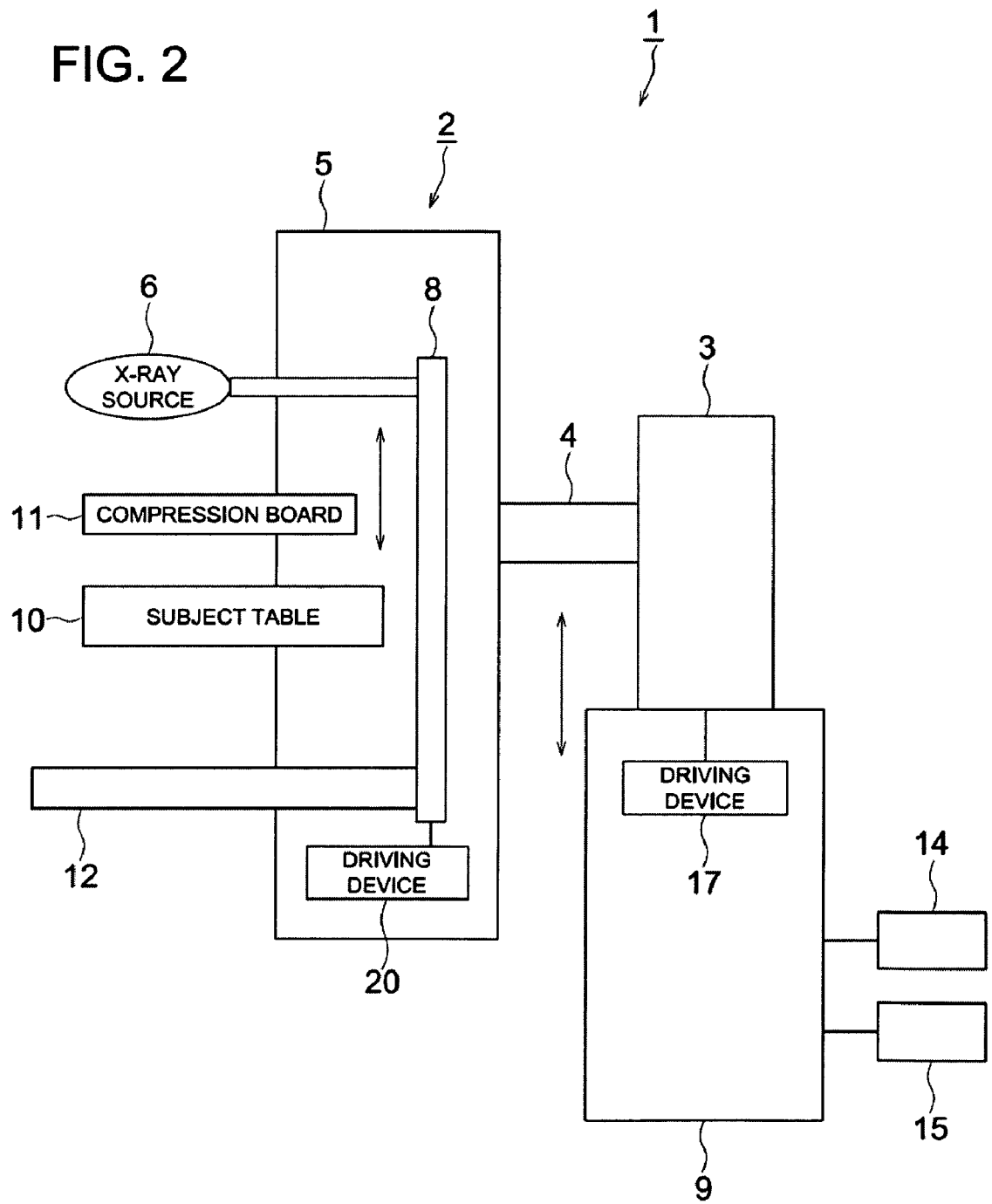
FIG. 2 is a diagram showing schematically an internal structure of radiographing apparatus main body section 2 of breast image radiographing apparatus 1.

Each of FIGS. 1 and 2 shows an example of the structure of the breast image radiographing apparatus 1. FIG. 1 is a diagram showing an example of a structure in external appearance of the breast image radiographing apparatus 1, and FIG. 2 is a diagram wherein an internal structure of radiographing apparatus main body section 2 of the breast image radiographing apparatus 1 shown in FIG. 1 is shown schematically. Incidentally, in FIG. 2, operation device 14, power source section 15, driving device 17 and driving device 20, which is an adjusting device, are connected to control device 16 (illustrated in FIG. 3) which is a control device of main body section 9, however the control device 16 is not illustrated here. As shown in FIG. 1, supporting base table 3 is provided on main body section 9 to be capable of ascending and descending in the breast image radiographing apparatus 1, and on the supporting base table 3, there is supported radiographing apparatus main body section 2 through the supporting shaft 4 provided on the supporting base table 3. The supporting base table 3 is driven by the driving device 17 composed of a motor and others to ascent and descend. The radiographing apparatus main body section 2 is made to be capable of ascending and descending by ascending and descending of the supporting base table 3 by the driving device 17, and is made to be capable of rotating around the aforesaid supporting shaft 4 by the driving device 17.

On the upper portion of the radiographing apparatus main body section 2, radiation source 6 for emitting a radiation is provided, and this radiation source 6 is connected to power source section 15 that is connected to main body section 9 through supporting shaft 4 and supporting base table 3. This radiation source 6 is arranged so that tube voltage and tube current may be applied on the radiation source 6 by the power source section 15. On a radiation orifice of the radiation source 6, there is provided an aperture hole of aperture device 7 that serves as an irradiation field adjusting device which adjusts radiation irradiation field, to be capable of opening and closing.

It is preferable that a rotating anode X-ray tube serves as the radiation source 6. In this rotating anode X-ray tube, X-ray is generated when an electron beam emitted from a cathode hits an anode. This X-ray is incoherent like natural light, and it is not parallel X-ray, but is divergent light. When the electron beam continues hitting the fixed position on the anode, the anode is damaged by heat generation. Therefore, an anode is rotated in an X-ray tube used in general, to prevent a decrease of the life of the anode. An electron beam is caused to hit a plane surface in a prescribed size on an anode, and X-ray thus generated is emitted from the plane surface in prescribed size on the anode to subject H. This plane surface is called a focus. When a focus is a regular square, focus size D (μm) is a length of its side, when a focus is a rectangle or a polygon, focus size D (μm) is a length of its shorter side, and when a focus is a circle, focus size D (μm) is a length of its diameter.

The greater the focus size D is, the more an amount of radiation dose irradiated is. Since an amount of radiation dose equal to or more than a certain amount is required to transmit a human body, it is preferable, in the breast radiographing apparatus 1, that the focus size D capable of irradiating an amount of radiation dose required for radiographing a human body satisfies D≧30 (μm).

On the lower portion of radiographing apparatus main body section 2, detector holding section 12 representing a detector holding device that holds a cassette storing stimulable phosphor sheet, for example, is mounted facing radiation source 6 at the position that is below the subject table 10 and is extending almost vertically from radiation source 6, as a radiation image detector that detects radiation having transmitted through subject H. A topmost surface of the radiation image detector held on the detector holding section 12 agrees with a topmost surface of the detector holding section 12. The radiation source 6 and the detector holding section 12 are mounted on holding member 8 representing a holding device, as shown in FIG. 2, and distance L (R1+R2 which will be described later) between the radiation source 6 and the detector holding section 12 is maintained to be constant by this holding member 8. The holding member 8 is driven by driving device 20 that is composed of a motor and others to be capable of ascending and descending, and ascending and descending of the holding member 8 by driving device 20 cause the radiation source 6 and the detector holding section 12 to ascend and descend while keeping a constant distance. It has been found after keen studies that L≧0.95 (m) is preferable for the distance L between the radiation source 6 and the detector holding section 12, from the viewpoint of visibility in the case of outputting radiographed images (see FIG. 6).

As a radiation image detector, screen (intensifying screen)/film and FPD (flat panel detector), for example, may also be used, in addition to the aforesaid cassette storing the stimulable phosphor sheet.

At the position that is below the radiation source 6 and is above the detector holding section 12, and is extending almost vertically from the radiation source 6, in the radiographing apparatus main body section 2, there are provided subject table 10 that holds subject H from the bottom and compression board 11 for fixing subject H by pressing it from the upper side. The subject table 10 is fixed on holder 5 of the radiographing apparatus main body section 2 as shown in FIG. 2, and it ascends and descends depending on ascending and descending of the radiographing apparatus main body section 2 conducted by driving device 17. Due to this, it is possible to adjust a height of subject table 10 depending on a position of subject H (breast position). The compression board 11 is structured to be capable of ascending and descending along an unillustrated supporting shaft provided in the radiographing apparatus main body section 2.

A position of the compression board 11 is detected by position detecting section 18 (illustrated in FIG. 3), and is outputted to control device 16 of maim body section 9. Those which can be employed as position detecting section 18 include a detector of a type of photometry using infrared rays, and a detector of a type of position-distinction wherein a linear resistance is provided on a rail of a supporting shaft for sliding the compression board, and a position is distinguished by a value of resistance.

On the surface opposite to the surface of the detector holding section 12 facing subject table 10, there is provided radiation dose detector 13 that detects an amount of radiation dose irradiated, and the amount of radiation dose detected by the radiation dose detector 13 is outputted to control device 16 of main body section 9.

Figure 3:
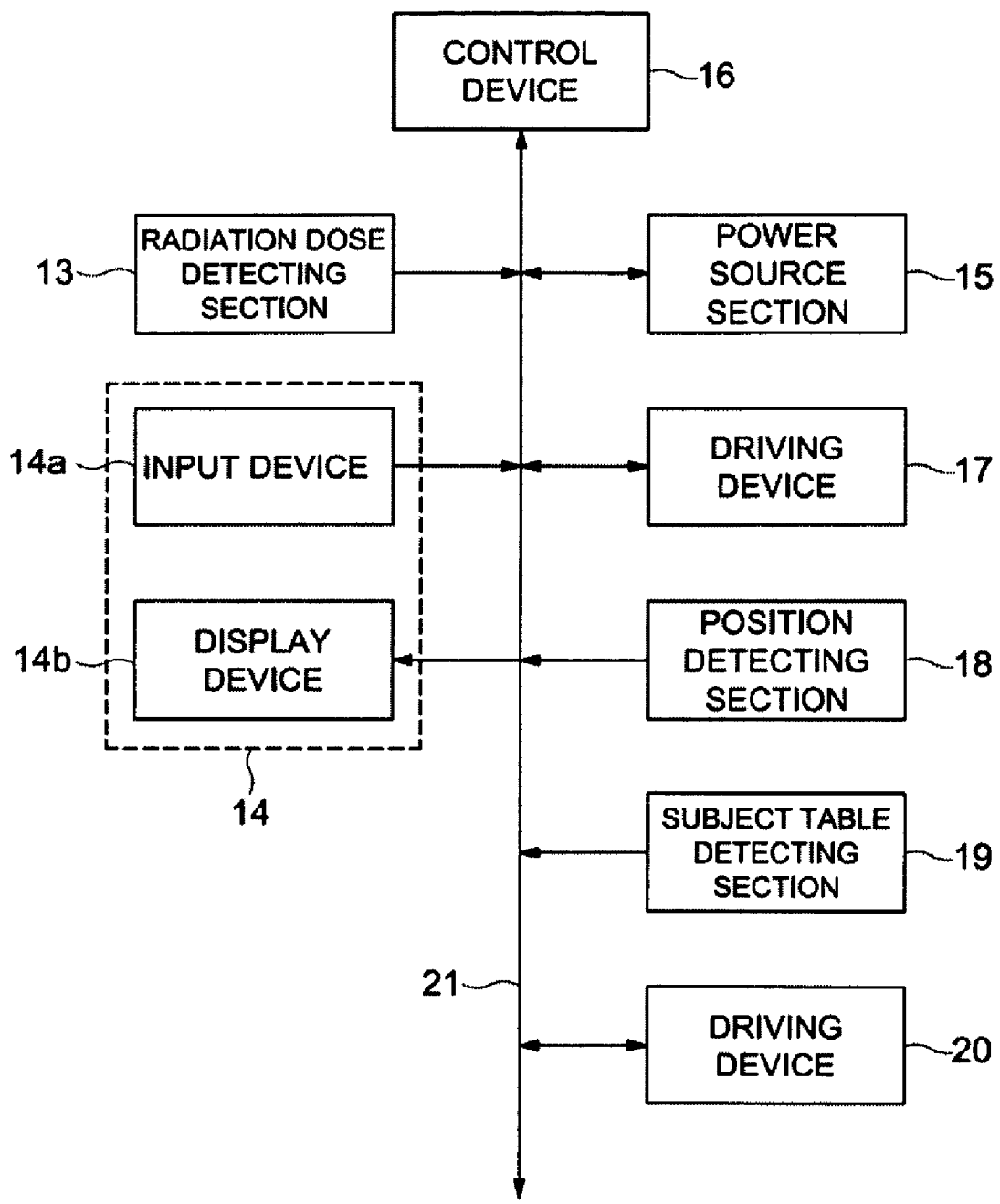
FIG. 3 is a block diagram showing a functional structure of breast image radiographing apparatus 1.

The main body section 9 is equipped with control device 16 composed of CPU (Central Processing Unit), ROM (Read Only Memory) and RAM (Random Access Memory). FIG. 3 shows an example of a functional structure of breast image radiographing apparatus 1. As shown in FIG. 3, the control device 16 is connected, through bus 21, with radiation dose detector 13 that detects an amount of irradiated radiation, operation device 14 having therein input device 14a equipped with a key board and a touch panel that inputs radiographing conditions, position adjustment switch for adjusting a position of subject table 10 (an upper adjusting switch to adjust upward and a lower adjusting switch to adjust downward) and a setting device that sets enlargement factor for radiographing, and display device 14b such as CRT display and a liquid crystal display, power source section 15 representing a source of power for an apparatus, driving device 17 that conducts ascending and descending of the radiographing apparatus main body section 2 by ascending and descending of supporting base table 3 and rotation of the radiographing apparatus main body section 2, position detecting section 18 that detects a position of compression board 11, subject table detecting section 19 that detects mounting of subject table 10 and its size information and with driving device 20, conducting ascending and descending of holding member 8. In ROM of control device 16, there are stored control programs for controlling each section of breast image radiographing apparatus 1 and various types of processing programs, and CPU controls operations of each section of radiographing apparatus 1 on a supervising basis through cooperations of the control program and various types of processing programs, to conduct phase contrast radiographing. For example, when a position adjusting switch of input device 14a is depressed, CPU controls driving device 17 responding to this depression, to adjust a position of subject table 10, and a position of compression board 11 is adjusted by an operator such as a radiographing technician, so that subject H is pressed and fixed and when an enlargement factor in phase contrast radiographing is inputted by input device 14a, driving device 20 is controlled to raise and lower the holding member 8 in accordance with positions of subject table 10 and compression board 11 and with inputted enlargement factor, thus, a relative distance of subject table 10 to radiation source 6 and to radiation image detector is adjusted. Then, if radiographing is instructed by input device 14a, tube voltage and tube current are impressed on radiation source 6 by power source section 15, to irradiate subject H with radiation, and power source section 15 stops irradiation with radiation coming from radiation source 6, when an amount of radiation dose inputted from radiation dose detector 13 arrives at an amount of radiation dose set in advance.

Figure 4:
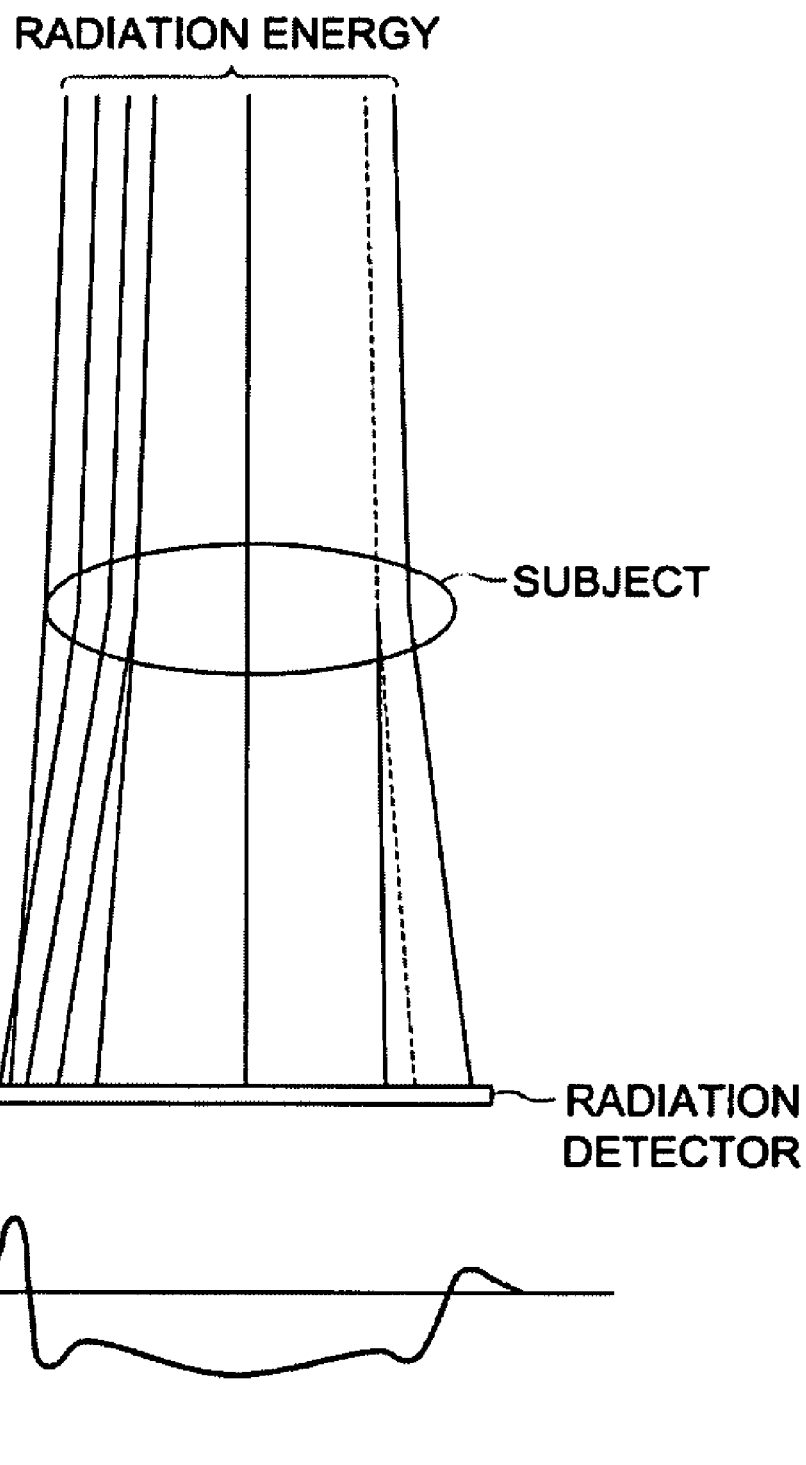
FIG. 4 is a diagram for illustrating a principle of phase contrast radiographing.

Now, a principle of phase contrast radiographing will be described as follows, referring to FIG. 4. The phase contrast radiographing is one wherein an edge enhancement (refraction contrast enhancement) image caused by refraction of radiation is obtained as shown in FIG. 4, by providing fixed distance R2 between subject H and a radiation image detector. As is drawn schematically in FIG. 4, when radiation passes through an object, the radiation is refracted by the object, and radiation density inside a boundary of the object becomes to be low, while, in the outside of the object, the radiation overlaps with radiation that has not passed through the object, resulting in raised radiation density. In this way, an edge that is a subject boundary portion is enhanced as an image. This is a phenomenon caused by a difference in terms of a refractive index for radiation between the object and air. This is an edge enhancement image.

Not only the edge enhancement at a boundary between air and a subject shown on a principle basis, but also the same effect is obtained at the boundary portion where refractive indexes are different, even inside the object. The subject boundary portion mentioned in the present invention can be expressed as a portion of a boundary with substances where refractive indexes for radiation are different from each other.

With respect to preferable sensitivity area in practical range and to an apparatus size for obtaining edge enhancement images in medical facilities, when focus size D (μm) is 30 (μm) or more, the aforesaid area is one where distance R1 from radiation source 6 to subject H satisfies an expression of R1≧(D−7)/200 (m), and distance R2 between subject H and a radiation image detector is 0.15 m or more, which has been known (see Unexamined Japanese Patent Application Publication No. 2001-91479). In this case, D to be substituted in expression of R1≧(D−7)/200 (m) represents a numerical value where a focus size is expressed with a unit of μm, and for example, if focus size D is 30 (μm), it results in R1≧(30−7)/200=0.115 (m).

When R1 is smaller than the distance shown with an expression of R1≧(D−7)/200 (m), it is difficult to obtain edge enhancement images, or it results in difficult recognition. Further, when R1 grows greater, radiation intensity becomes weak and a broader space is required.

By employing the structure wherein distance R2 from subject H to a radiation image detector is 0.15 (m) or more, scattered radiation that comes from subject H and deteriorates sharpness of a radiation image is removed, and edge enhancement is made to be easily recognized.

If R2 is made to be 0.15 m or more, enlargement radiographing with Enlargement factor=(R1+R2)/R1 results. In this case, with respect to R1, its starting point is a position of focus of radiation source 6, and its position is shown clearly on ordinary radiation source 6 available on the market. Further, a terminal point is a center line of subject H fixed by subject table 10 that fixes a subject position, and in this case, a center line of subject H is represented by a position which is equally located from subject table 10 and compression board 11. With respect to R2, the starting point is a center line of subject H, and the terminal point is an uppermost surface of a plane, that receives radiation, of a radiation image detector, that is, an uppermost surface of detector holding section 12.

Breast image radiographing apparatus 1 satisfies Focus size D≧30 (μm) so that an effect (edge enhancement effect) as the aforesaid phase contrast may be exhibited, and in the case of radiographing, a position of subject table 10 for each of radiation source 6 and a radiation image detector is adjusted by control device 16 within a range of satisfying (Distance R1 from radiation source 6 to subject H)≧(D−7)/200 (m) and satisfying (Distance R2 from subject H to radiation image detector)≧0.15 (m).

In other words, when radiographing conditions including a radiographing direction are inputted by input device 14a in the case of radiographing, control device 16 judges whether the inputted radiographing direction is one requiring rotation of radiographing apparatus main body section 2 or not, and when the inputted radiographing direction is one requiring the rotation of radiographing apparatus main body section 2, for example, in the case of MLO (Medio-Lateral Oblique) for radiographing a breast in the oblique direction, the whole of radiographing apparatus main body section 2 is rotated by a prescribed amount by driving device 17. When a position adjustment switch of input device 14a is pressed down, control device 16 controls driving device 17 responding to the aforesaid pressing down, to adjust a position of subject table 10. When a position of compression board 11 is adjusted by an operator such as a radiographing technician, to press and fix subject H with the compression board 11, and when enlargement factors (to select from 1.46 times, 1.75 times and 2.63 times in the present embodiment) in the case of phase contrast radiographing are inputted by input device 14a, the control device 16 specifies a position of subject H in accordance with an amount of movement of subject table 10 and position information coming from position detecting section 18, then, controls driving device 20 in accordance with positions of subject table 10 and compression board 11 and with inputted enlargement factors, and adjusts a relative distance of subject table 10 relative to radiation source 6 and a radiation image detector, by causing holding member 8 to ascend or descent. In this case, positions of radiation source 6 and detector holding section 12 wherein (R1+R2)/R1 is the inputted enlargement factor, are calculated, and holding member 8 is caused to ascend or descend to acquire required positions of radiation source 6 and detector holding section 12. Then, after radiographing is instructed by input device 14a, control device 16a causes power source section 15 to apply tube voltage and tube current on radiation source 6 to irradiate subject H with radiation. If an amount of radiation dose inputted from radiation dose detecting section 13 arrives at a radiation dose set in advance, irradiation by radiation coming from radiation source 6 is stopped by the power source section 15.

Meanwhile, adjustment of relative distance of subject table 10 relative to radiation source 6 and a radiation image detector is conducted in a range that satisfies R1≧(D−7)/200 (m) and R2≧0.15 (m). Control device 16 causes display device 14b to indicate an error message, when the inputted enlargement factor does not satisfy the aforesaid range.

As stated above, when control device 16 controls driving device 20 to cause holding member 8 to ascend or descend, an adjustment device that adjusts relative distances of subject table 10 to radiation source 6 and to a radiation image detector is realized.

Figure 5:
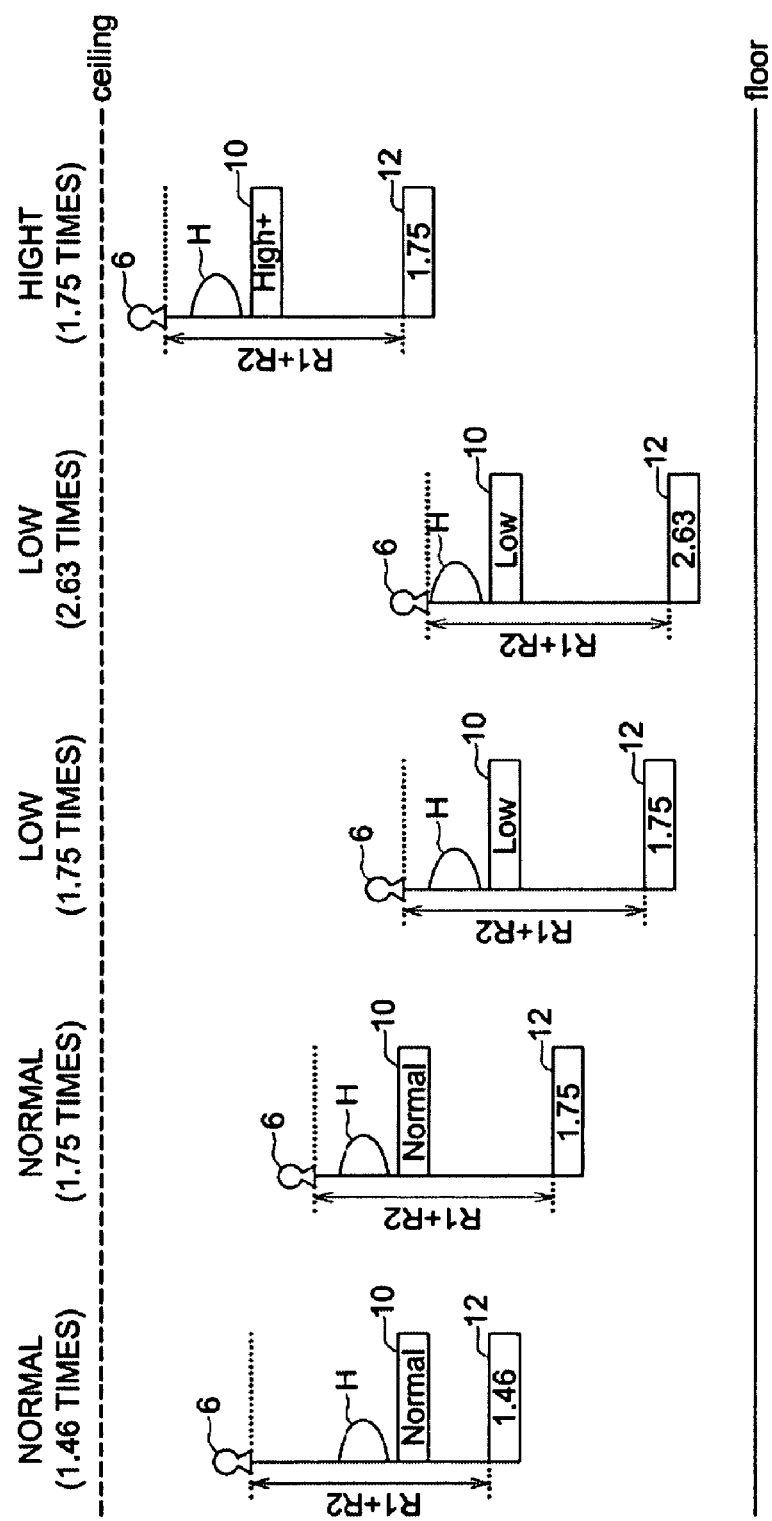
FIG. 5 is a diagram for showing schematically positional relationship for radiation source 6, subject H, detector holding section 12, a floor and a ceiling, in the case of radiographing a breast image by breast image radiographing apparatus 1.
Figure 7:
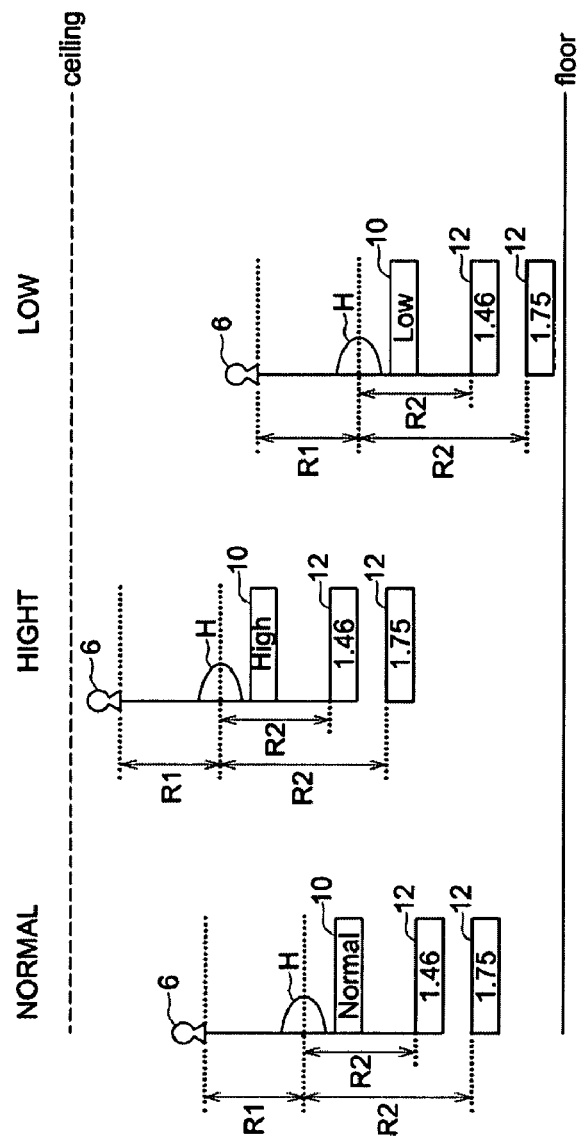
FIG. 7 is a diagram for showing schematically positional relationship for radiation source 6, subject H, detector holding section 12, a floor and a ceiling, in the case of radiographing a breast image in a conventional radiographic imaging apparatus for breast radiography.

FIG. 5 shows schematically positional relationship for radiation source 6, subject H, detector holding section 12 in the case of radiographing a breast image in breast image radiographing apparatus 1 in the present embodiment (numerals in the figure show an enlargement factor), and a floor and ceiling in a radiographing chamber where phase contrast radiographing is conducted. Since distance L of R1+R2 is constant even when an enlargement factor is changed in the present embodiment, as shown in FIG. 5, there is no problem wherein the enlargement factor that is growing greater requires more distance between a floor surface and detector holding section 12, and if the subject position is low, the aforesaid distance cannot be secured, and an enlargement factor that makes radiographing possible is restricted, as in the past. As a result, a range of subject positions that make phase contrast radiographing possible can be expanded, and the breast image radiographing apparatus in the invention can be applied on more patients.

(Evaluation of Visibility Concerning Breast Image Radiographing Apparatus 1)

Distance L between radiation source 6 and detector holding device 12 and results of evaluation of visibility in radiographed images will be described as follows.

FIG. 6 shows results of evaluation of visibility for each radiographed image resulting from breast radiographing conducted under the condition where R1+R2 representing distance L between radiation source 6 and detector holding device 12 was 1555 (mm), 1140 (mm), 950 (mm) and 750 (mm), and an enlargement factor for each R1+R2 was 1.75 times and 1.46 times respectively. Evaluation was conducted through visual check on a 4-level evaluation basis, including A: Excellent B: Good C: Normal, So-so (judged to be permissible level for diagnoses) and D: Bad.

The evaluation was conducted according to each item in FIG. 6.

For the evaluation, a pre-production sample made by Konica Minolta Holdings, Inc. was used as breast image radiographing apparatus 1, and regius plate RP-5PM and regius cassette RC-110M made by the same company were used as a radiation image detector. Focus size D was made to satisfy D=100 (μm). A radiation image detector after radiographing a breast was read by regius model 190 manufactured by Konica Minolta Holdings, Inc. at a reading pixel pitch of 43.75 (μm), and images thus read were outputted by drypro model 793 at a writing pitch of 25 (μm). In this case, each pixel of read image and each pixel of outputted image were made to correspond to be 1:1 and were outputted without conducting interpolation processing, and images with enlargement factor of 1.75 times were outputted at a life size (full scale), and images with enlargement factor of 1.46 times were outputted at 0.83 times of a life size. Further, in the case of radiographing at an enlargement factor of 1.46 times, enlargement interpolation processing of 1.25 times was conducted, and output was conducted at writing pitch of 25 (μm) by using an enlarged and interpolated image. However, a difference of visibility from the result shown in FIG. 6 was not observed.

In this case, a factor contributing to an item "output" is a distance of R1. In general, when R1 is large, and an amount of radiation dose per a unit of time arriving at the radiation image detector is little, sufficient density cannot be obtained.

A factor contributing to an item "uniformity" is a distance of R1. In general, when R1 is too small, unevenness is caused and uniformity is lowered, because it is impossible to irradiate the total surface of the radiation image detector with radiation.

A factor contributing to "sharpness" and "graininess" is an enlargement factor, and in general, the greater the enlargement factor is, the better an image is.

A factor contributing to "scattered radiation content rate" is R2, and in general, the greater the R2 is, the more the scattered radiations are removed and the better an image is.

A factor contributing to "phase contrast effect (edge enhancement effect)" is an enlargement factor and R2, and when both an enlargement factor and R2 are made to be greater, more effect of phase contrast is obtained, resulting in better images.

"Overall judgment" is a result of evaluation for visibility of the whole of an image.

When R1+R2≧950 (mm) resulted as the results of evaluation of visibility, there was obtained an evaluation that both of a phase contrast effect and an overall evaluation are allowed to be used for diagnoses. That is, it was confirmed that an image allowed to be used for diagnoses can be obtained in a radiographic imaging apparatus that conducts phase contrast radiographing by fixing R1+R2, under the condition of R1+R2≧950 (mm).

In the meantime, though there was shown an example of focus size D=100 (μm) in the aforesaid results of evaluations, the same effect can be exhibited even when D is one other than 100 (μm), provided that D is 30 (μm) or more.

Second Embodiment

Next, Second Embodiment will be described. With respect to those other than the descriptions below, they are the same as those in First Embodiment.

In the present embodiment, a radiation image detector of a type of 14×17 (inches) is used.

Meanwhile, as a radiation image detector, a screen (intensifying screen)/film and an FPD (Flat Panel Detector), for example, may also be used, in addition to the cassette storing the aforesaid stimulable phosphor sheet.

Figure 8:
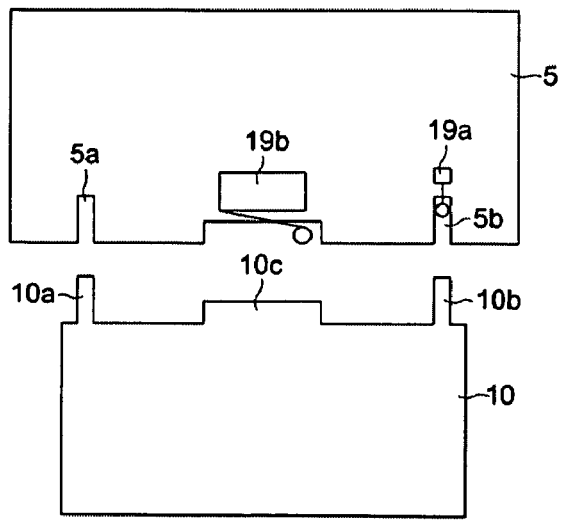
FIG. 8 is a schematic diagram (a cross section) wherein subject table 10 and a subject table mounting portion of holder 5 are viewed from the above.

Subject table 10 is constituted to be capable of being attached to and detached from holder 5 of radiographing apparatus main body section 2, and an operator such as a radiographing technician who conducts radiographing can select subject table 10 of one size from subject tables 10 of sizes of 2 or more, in accordance with a size of subject H to be radiographed, to attach it on the radiographing apparatus main body section 2. In the present embodiment, two types of subject tables 10 having sizes respectively of 18×24 (cm) and 24×30 (cm) can be attached. FIG. 8 is a schematic diagram (sectional view) wherein subject table 10 and a subject table mounting section of holder 5 are viewed from the upper portion. As shown in FIG. 8, subject table 10 has protrusions 10a and 10b for mounting on holder 5, and when inserting protrusion 10a in recessed portion 5a that is formed on holder 5 and when inserting protrusion 10b in recessed portion 5b that is formed on holder 5, the subject table 10 can be mounted on holder 5.

The subject table 10 mounted on holder 5 ascends and descends, following ascending and descending of radiographing apparatus main body section 2 that is driven by driving device 17. Owing to this, a height of a subject table can be adjusted in accordance with a position of a subject (breast position). The mounting of subject table 10 and a size of the subject table 10 mounted on radiographing apparatus main body section 2 are detected by subject table detecting section 19 (illustrated in FIG. 3) representing a subject table size acquiring device, and its size information is outputted to control device 16 of main body section 9. As the subject table detecting section 19, a microswitch or the like can be used. For example, as shown in FIG. 8, if microswitches 19a and 19b both representing subject table detecting section 19 are provided on folder 5, and if subject table 10 for a size of 18×24 (cm) is made to be of a structure to have protrusion 10c, and subject table 10 for a size of 24×30 (cm) is made to be of a structure to have no protrusion 10c, microswitch 19a is turned on when either one of subject table 10 is mounted, and microswitch 19b is turned on only when subject table for 18×24 (cm) is mounted. Owing to this, it is possible to detect the mounting of subject table 10 and its size. Compression board 11 is constituted to be capable of ascending and descending along an unillustrated supporting shaft that is provided in radiographing apparatus main body section 2.

In ROM of control device 16 shown in FIG. 3, there are stored control program for controlling each section of breast image radiographing apparatus 1 and various types of processing programs, and CPU controls operation of each section of radiographing apparatus 1 on a supervising basis, through cooperation with this control program and various types of processing programs, and conducts phase contrast radiographing.

For example, CPU reads out position control processing A programs stored in ROM to RAM to operate position control processing A (see FIG. 9) which will be described later, and controls driving device 20 based on a size of the mounted subject table 10 to adjust relative distances from subject table 10 by moving the radiation source 7 and detector holding section 12. Then, after radiographing is instructed by input device 14a, CPU performs radiographing processing, then, causes power source section 15 to impress tube voltage and tube current on radiation source 6, to irradiate subject H with radiation, and causes the power source section 15 to stop irradiation of radiation coming from radiation source 6, when an amount of radiation dose inputted from radiation dose detecting section 13 arrives at an amount of radiation dose set in advance.

In Second Embodiment, it is assumed that breast image radiographing apparatus 1 radiographs at any one of enlargement factors (radiographing enlargement factor) of 1.46 times, 1.75 times and 2.63 times.

Operations of the breast image radiographing apparatus 1 in Second Embodiment will be described.

Figure 9:
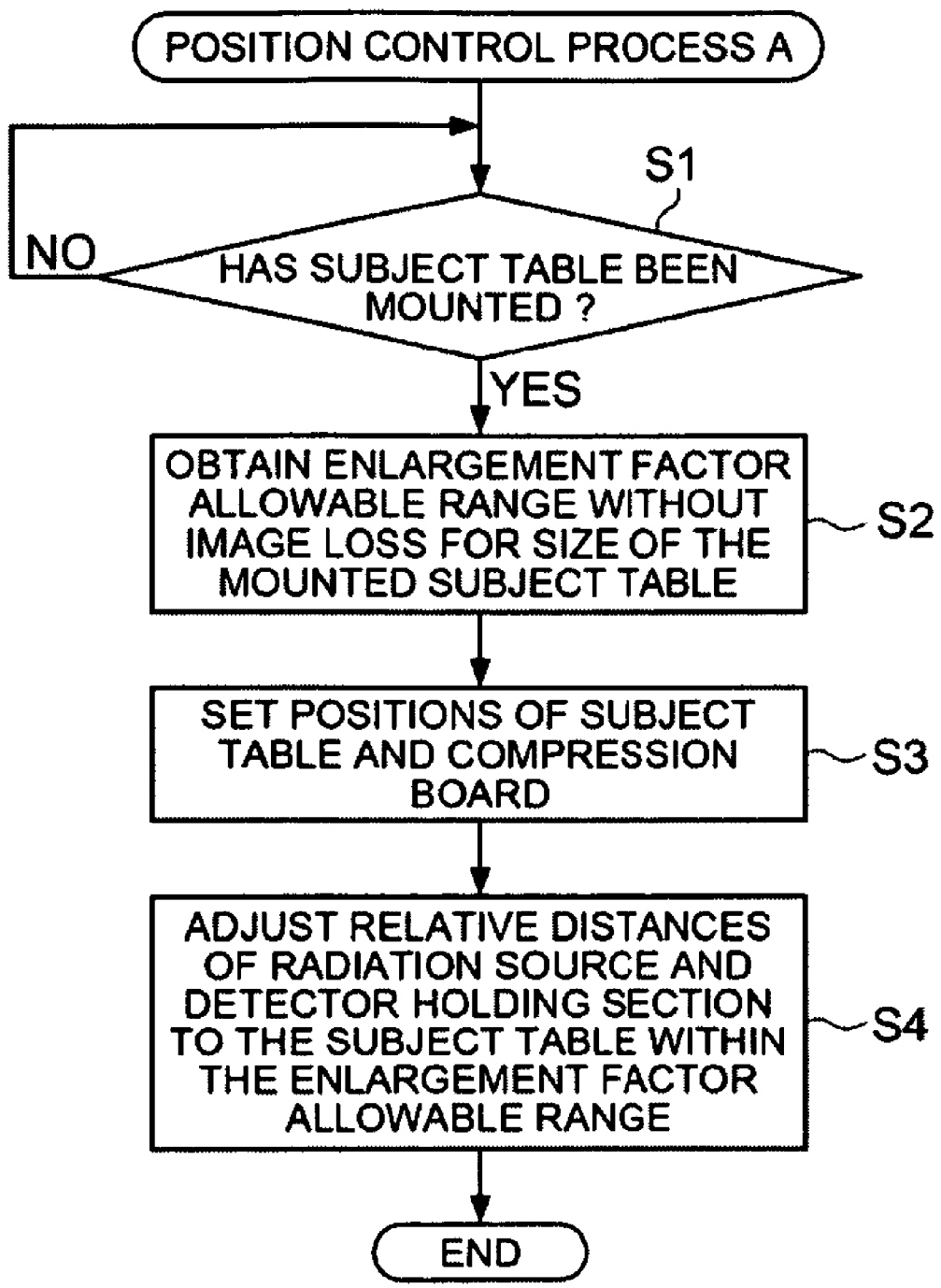
FIG. 9 is a flow chart showing position control processing A that is conducted by control device 16 in FIG. 3.

FIG. 9 shows position control processing A performed by control device 16. Now, the position control processing A will be described as follows, referring to FIG. 9.

When subject table detecting section 19 detects that subject table 10 is mounted, and subject table size information is inputted (step S1; YES), a range of enlargement factor (allowable range of enlargement factor) in which the whole of subject H can be radiographed without image missing at a size of the mounted subject table, in other words, a range of enlargement factor (allowable range of enlargement factor) in which a radiation image of the whole of subject H held by subject table 10 can be detected by radiation image detector held on detector holding section 12, is obtained (step S2), based on subject table size information inputted from subject table detecting section 19.

As stated above, a subject table size is 18×24 (cm) or 24×30 (cm) in the present embodiment. Since a radiation image detector is 14×17 (inch) in this case, when a subject table size is 18×24 (cm), if radiographing is conducted at an enlargement factor of 2.65, a part of a radiation image that has passed through a range of the whole of subject table 10 may not be covered by the radiation image detector, thus, a part of an image of subject H is lost when subject H is arranged up to the margin on subject table 10. Therefore, in the case where a subject table size is 18×24 (cm), the allowable range of enlargement factor is up to 1.75 times. Further, when a subject table size is 24×30 (cm), if radiographing is conducted at an enlargement factor of 2.65 or 1.75, a part of a radiation image that has passed through a range of the whole of subject table 10 may not be covered by the radiation image detector, thus, a part of an image of subject H is lost when subject H is arranged up to the margin on subject table 10. Therefore, in the case where a subject table size is 24×30 (cm), the allowable range of enlargement factor is up to 1.46 times.

The allowable range of the enlargement factor is an enlargement factor that satisfies "longitudinal size of subject table 10×enlargement factor≦longitudinal size of radiation image detector" and "lateral size of subject table 10×enlargement factor≦lateral size of radiation image detector". This can be obtained either by calculating for each performance of position control processing A, or by referring to the table of correspondence between subject table size information and enlargement factor that is stored in a memory device such as ROM.

Next, a position of subject table 10 and a position of compression board 11 are adjusted, and positions of subject table 10 and compression board 11 are set (step S3). Specifically, when input device 14a is operated by an operator such as a radiographing technician and radiographing conditions including a radiographing direction are inputted, the inputted radiographing direction is judged whether it is a radiographing direction requiring a rotation of radiographing apparatus main body section 2 or not. When it is a radiographing direction requiring a rotation, for example, when it is MLO (Medio-Lateral Oblique) that is radiographing a breast in the oblique direction, driving device 17 is controlled and the whole of radiographing apparatus main body section 2 is rotated by a prescribed amount. When a position adjustment switch of input device 14a is operated, driving device 17 is controlled depending on the operation of the position adjustment switch, and a position of subject table 10 is adjusted. Further, a position of compression board 11 is adjusted by an operator such as a radiographing technician, and subject H is pressed and fixed. After the adjustment, instructions for setting subject table 10 and compression board 11 to the adjusted positions are inputted from input device 14a, thus, setting is completed.

After positions for the subject table 10 and the compression board 11 are set, driving device 20 is controlled, and relative distances of the subject table 10 to radiation source 6 and to a radiation image detector are adjusted so that an enlargement factor may be within the allowable range of the enlargement factor obtained in step S2 (step S4). For example, an enlargement factor of default is set in advance, and when an enlargement factor of default is within the allowable range of the enlargement factor, relative distances of the subject table 10 to radiation source 6 and to a radiation image detector are calculated respectively in accordance with enlargement factor of default. Then, when driving device 20 is controlled, holding member 8 is moved to the position where a distance from radiation source 6 to subject table 10 and a distance from a radiation image detector to subject table 10 become the calculated distances, and relative distances respectively from subject table 10 to radiation source 6 and from subject table 10 to a radiation image detector are adjusted. When an enlargement factor of default exceeds the allowable range of the enlargement factor, a relative distance of subject table 10 to radiation source 6 and a relative distance of subject table 10 to a radiation image detector are calculated, depending on the maximum enlargement factor in the allowable range of the enlargement factor. Then, when driving device 20 is controlled, holding member 8 is moved to the position where a distance from radiation source 6 to subject table 10 and a distance from a radiation image detector to subject table 10 become the calculated distances, and relative distances respectively from subject table 10 to radiation source 6 and from subject table 10 to a radiation image detector are adjusted.

When the aforesaid position control processing A comes to an end, and radiographing instruction is inputted, radiographing processing is carried out, and tube voltage and tube current are applied on radiation source 6 by power source section 15, and subject H is irradiated with radiation so that radiographing is conducted.

As described above, in breast image radiographing apparatus 1 in Second Embodiment, a range of enlargement factor is determined based on a size of the mounted subject table, and radiographing is conducted with an enlargement factor within this range. Thus, the whole of a subject can be made to be within a range for radiographing, and image missing can be prevented.

Further, though a size of a radiation image detector is made to be of one type of 14×17 (in.) in the aforesaid Second Embodiment, it is also possible to employ the structure wherein a radiation image detector that is compatible with two or more sizes can be mounted. In this case, it is either possible to output a size of the mounted radiation image detector to control device 16 by using a sensor that detects a detector size through photometry using infrared light as a detector size acquiring device, for example, or possible to output detector size information to control device 16 by providing a bar code showing a detector size at a prescribed position of a radiation image detector and by providing a bar code reader at a position of detector holding section 12 facing a bar code provided on a radiation image detector when mounting the radiation image detector, and by reading a detector size of the mounted radiation image detector by the bar code reader, when the radiation image detector is mounted on the detector holding section 12. When performing position control processing A in control device 16, an allowable range of enlargement factor may be calculated based on the inputted subject table size information and detector size information.

Third Embodiment

Next, Third Embodiment will be described. Since the structure of Third Embodiment is substantially the same as that of Second Embodiment, the description therefore is omitted here, and operations in Third Embodiment will be described.

Figure 10:
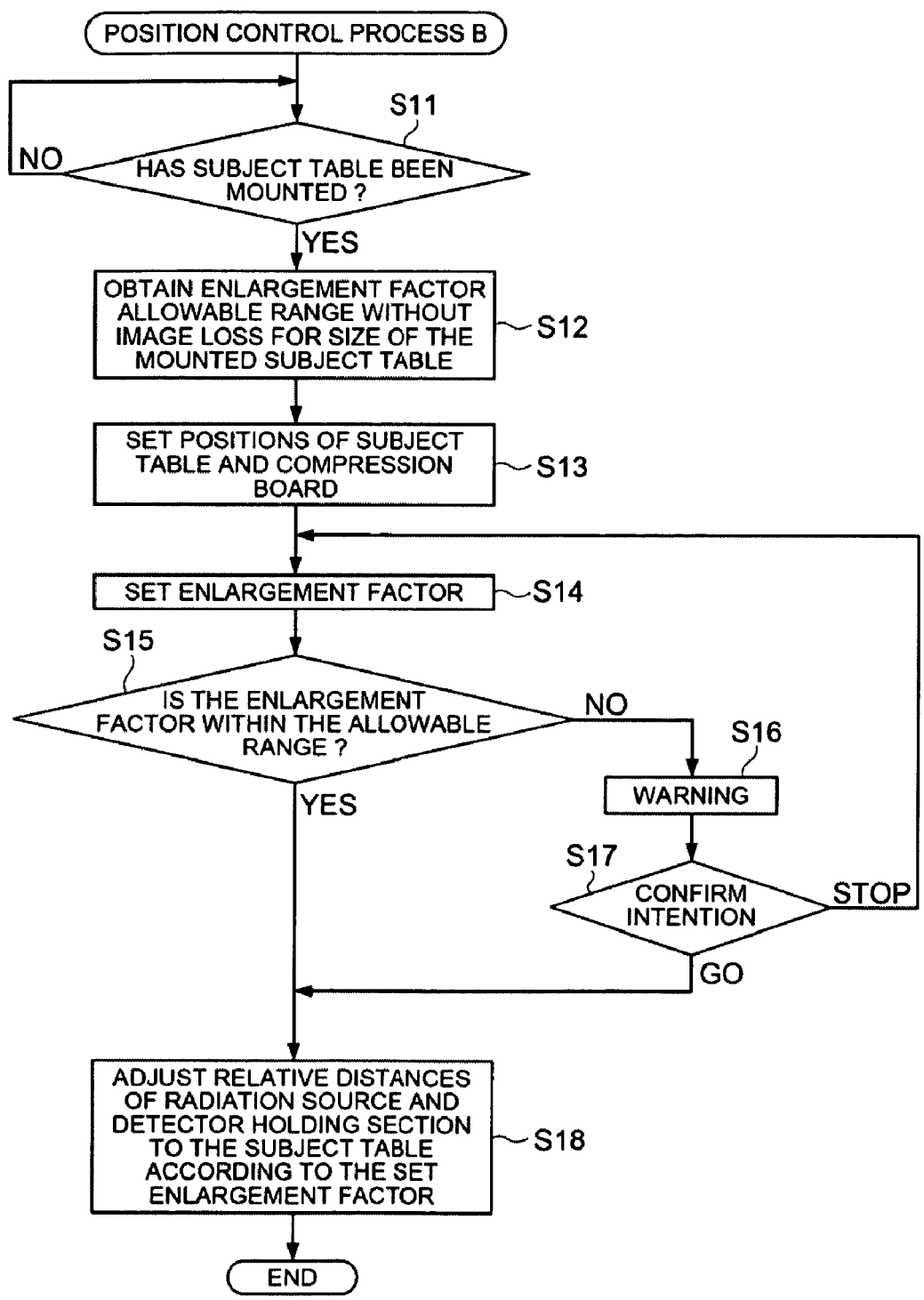
FIG. 10 is a flow chart showing position control processing B that is conducted by control device 16 in FIG. 3.

FIG. 10 shows position control processing B that is carried out by control device 16. The position control processing B will be described as follows, referring to FIG. 10.

When subject table detecting section 19 detects that subject table 10 is mounted, and when subject table size information is inputted (step S11; YES), a range of enlargement factor (allowable range of enlargement factor) that is capable of radiographing without image missing at a size of mounted subjective table, that is, capable for the radiation image of the whole of subject H held by subject table 10 to be detected by a radiation image detector held by detector holding section 12 is acquired based on the subject table size information inputted from the subject table detecting section 19 (step S12).

As stated above, a subject table size is 18×24 (cm) or 24×30 (cm) in the present embodiment. Since a radiation image detector is 14×17 (inch) in this case, when a subject table size is 18×24 (cm), if radiographing is conducted at an enlargement factor of 2.65, a part of a radiation image that has passed through a range of the whole of subject table 10 may not be covered by the radiation image detector, thus, a part of an image of subject H is lost when subject H is arranged up to the margin on subject table 10. Therefore, in the case where a subject table size is 18×24 (cm), the allowable range of enlargement factor is up to 1.75 times. Further, when a subject table size is 24×30 (cm), if radiographing is conducted at an enlargement factor of 2.65 or 1.75, a part of a radiation image that has passed through a range of the whole of subject table 10 may not be covered by the radiation image detector, thus, a part of an image of subject H is lost when subject H is arranged up to the margin on subject table 10. Therefore, in the case where a subject table size is 24×30 (cm), the allowable range of enlargement factor is up to 1.46 times.

The allowable range of the enlargement factor is an enlargement factor that satisfies "longitudinal size of subject table 10×enlargement factor≦longitudinal size of radiation image detector" and "lateral size of subject table 10×enlargement factor≦lateral size of radiation image detector". This can be obtained either by calculating for each performance of position control processing, or by referring to the table of correspondence between subject table size information and enlargement factor that is stored in a memory device such as ROM.

Next, a position of subject table 10 and a position of compression board 11 are adjusted, and positions of subject table 10 and compression board 11 are set (step S13). Specifically, when input device 14a is operated by an operator such as a radiographing technician and radiographing conditions including a radiographing direction are inputted, the inputted radiographing direction is judged whether it is a radiographing direction requiring a rotation of radiographing apparatus main body section 2 or not. When it is a radiographing direction requiring a rotation, for example, when it is MLO (Medio-Lateral Oblique) that is radiographing a breast in the oblique direction, driving device 17 is controlled and the whole of radiographing apparatus main body section 2 is rotated by a prescribed amount. When a position adjustment switch of input device 14a is operated, driving device 17 is controlled depending on the operation of the position adjustment switch, and a position of subject table 10 is adjusted. Further, a position of compression board 11 is adjusted by an operator such as a radiographing technician, and subject H is pressed and fixed. After the adjustment, instructions for setting subject table 10 and compression board 11 to the adjusted positions are inputted from input device 14a, thus, setting is completed.

When an enlargement factor (radiographing enlargement factor) is set and inputted by input device 14a after positions of subject table 10 and compression board 11 are set (step S14), the set enlargement factor is judged whether it is within an allowable range of enlargement factor obtained in step S12 or not (step S15). When the set enlargement factor exceeds the allowable range of enlargement factor (step S15; NO), display device 14b which serves also as a warning device indicates a warning screen which warns an operator of a situation that the set enlargement factor exceeds an allowable range of enlargement factor, a part of an image of subject H is not covered by the radiation image detector and image missing is caused (step S16). When an operator wishes to continue radiographing at the same enlargement factor, the operator can adjust a position of subject H so that an image of a region of interest of a subject may be covered by a detector. Further, an intention-confirmation screen that designates whether continuing radiographing at the same enlargement factor or setting an enlargement factor again is indicated on display device 14b, and when radiographing prohibition signals are inputted from the intention-confirmation screen through designation for setting an enlargement factor again (step S17; STOP), the processing returns to step S14. When the enlargement factor is within an allowable range for radiographing (step S15; YES), or when radiographing permission signals are inputted through designation of continued radiographing from intention-confirmation screen (step S17; GO), relative distances of subject table 10 respectively to radiation source 6 and a radiation image detector are calculated depending on the set radiographing enlargement factor. Then, the holding member 8 is moved to the position where distances of subject table 10 respectively to radiation source 6 and a radiation image detector become the calculated distances, thus, relative distances of subject table 10 respectively to radiation source 6 and a radiation image detector are adjusted (step S18) and the present processing is terminated.

After the aforesaid position control processing B is terminated, and indication for radiographing is inputted, radiographing processing is carried out, and tube voltage and tube current are impressed on radiation source 6 by power source section 15, whereby, subject H is irradiated with radiation and radiographing is performed.

As described above, in breast image radiographing apparatus 1 in Third Embodiment, a range of enlargement factor that makes it possible to radiograph the whole of subject H without image missing is obtained based on size information of the mounted subject table, then, a warning of image missing is indicated when the set enlargement factor is not within this range, and a chance of resetting an enlargement factor is given to an operator, thus, image missing can be prevented. Further, when an operator gives a priority to the enlargement factor, it is also possible to continue radiographing, by using the same enlargement factor as it is. In this case, it is possible to prevent image missing in a region of interest, because the operator can adjust a subject so that an image of the region of interest may be covered by a detector.

Further, though a size of a radiation image detector is made to be of one type of 14×17 (in.) in the aforesaid Second Embodiment, it is also possible to employ the structure wherein a radiation image detector that is compatible with two or more sizes can be mounted. In this case, it is either possible to output a size of the mounted radiation image detector to control device 16 by using a sensor that detects a detector size through photometry using infrared light as a detector size acquiring device, for example, or possible to output detector size information to control device 16 by providing a bar code showing a detector size at a prescribed position of a radiation image detector and by providing a bar code reader at a position of detector holding section 12 facing a bar code provided on a radiation image detector when mounting the radiation image detector, and by reading a detector size of the mounted radiation image detector by the bar code reader, when the radiation image detector is mounted on the detector holding section 12. When performing position control processing A in control device 16, an allowable range of enlargement factor may be calculated based on the inputted subject table size information and on detector size information.

Fourth Embodiment

Next, Fourth Embodiment will be described. Fourth Embodiment is one wherein a radiation shading member that covers a space formed between subject table 10 and detector holding section 12 is provided in each of the aforesaid First-Third Embodiments. A description for Fourth Embodiment is the same as that for each of the aforesaid First-Third Embodiments except the description below.

Figure 11:
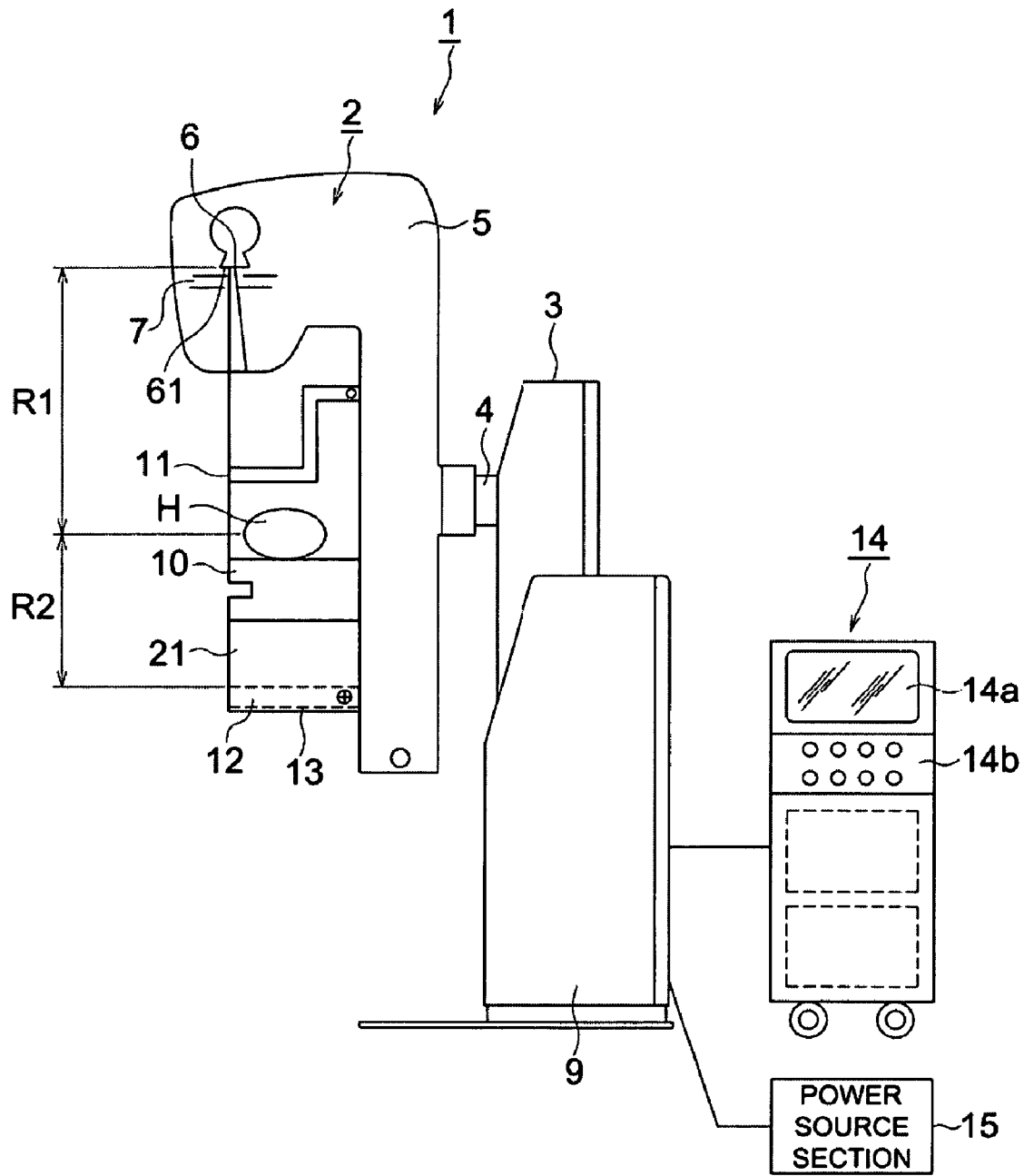
FIG. 11 is a diagram showing an example of a structure of breast image radiographing apparatus 1 on which the first radiation shading member 22 is mounted.
Figure 12:
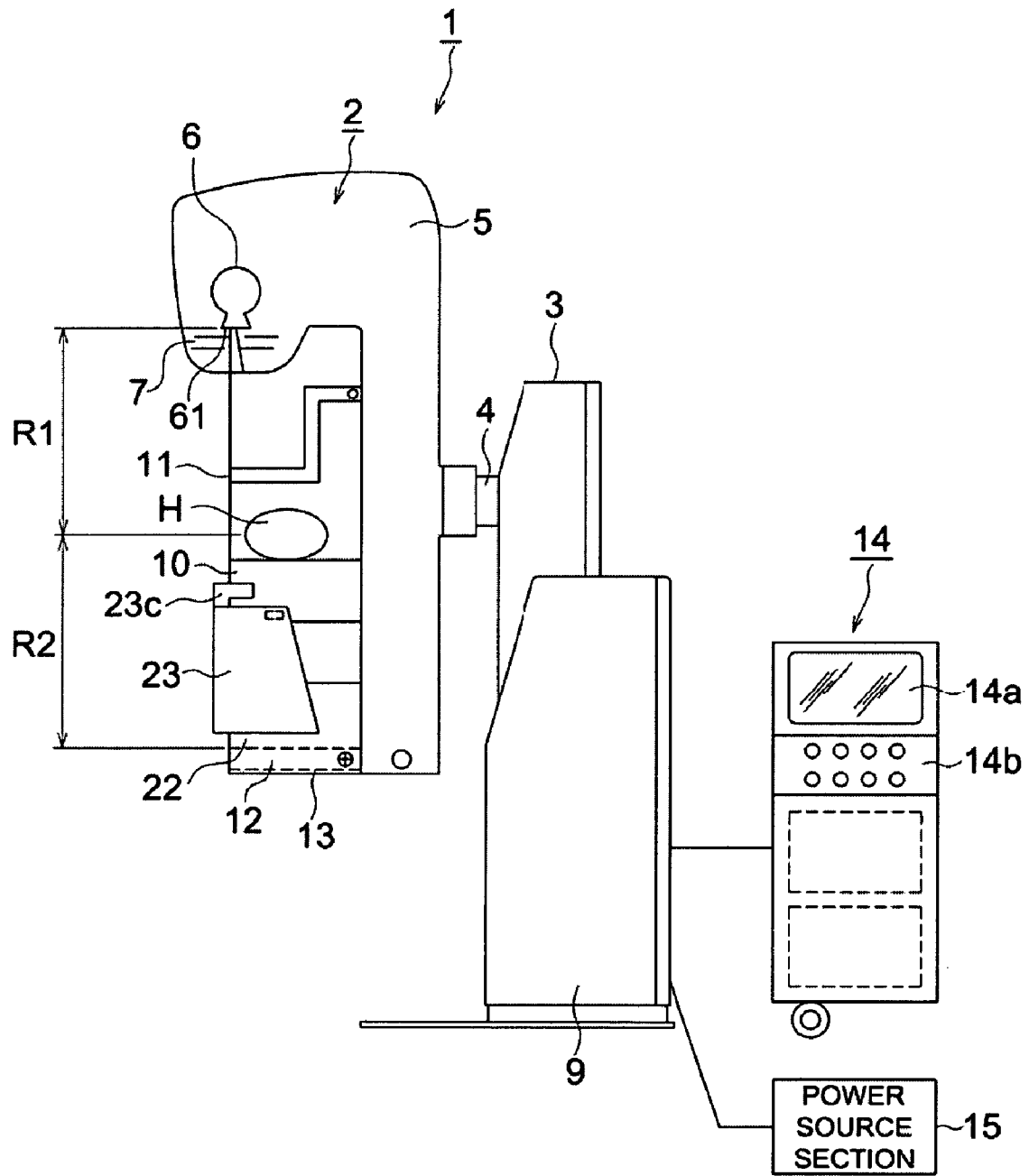
FIG. 12 is a diagram showing an example of a structure of breast image radiographing apparatus 1 on which the first radiation shading member 22 and the second radiation shading member 23 are mounted.

Each of FIG. 11 and FIG. 12 shows an example of a structure of a breast image radiographing apparatus 1 in Fourth Embodiment. FIG. 11 is a diagram showing an example of an external structure wherein the first radiation shading member 22 is mounted on breast image radiographing apparatus 1 shown in FIG. 1, while, FIG. 12 is a diagram showing an example of an external structure wherein the first radiation shading member 22 and the second radiation shading member 23 are mounted on breast image radiographing apparatus 1 shown in FIG. 1.

Detector holding section 12 has, on its front surface, attaching and detaching slot 12c (see FIG. 13) through which a radiation image detector is attached or detached, and the uppermost surface of the detector holding section 12 that is mounted from the attaching and detaching slot 12c and is held on the detector holding section 12 agrees with the uppermost surface of the detector holding section 12. On the subject table 10, there is provided engagement recess 10c that is to be engaged with engagement protrusion 23c (see FIG. 14) of the second radiation shading member 23. Further, on the left and right sides of the subject table 10, there are provided magnetic material metal plates 10a and 10b at positions corresponding respectively to magnet 23a and magnet 23b provided on an inner surface of the second radiation shading member 23 when engagement protrusion 23c of the second radiation shading member 23 is caused to engage with engagement recess 10c.

The aforesaid radiation shading member is made of lead or of lead glass. In addition to this, for enhancing the strength, resin and lead may be used to form a ply metal, or a plate of metal such as steel or stainless steel and lead may be used to form a ply metal.

In Fourth Embodiment, breast image radiographing apparatus 1 is constituted so that the first radiation shading member 22 and/or the second radiation shading member 23 may be attached or detached depending on an enlargement factor.

The first radiation shading member 22 and the second radiation shading member 23 will be described as follows, referring to FIG. 13-FIG. 15.

Figure 13:
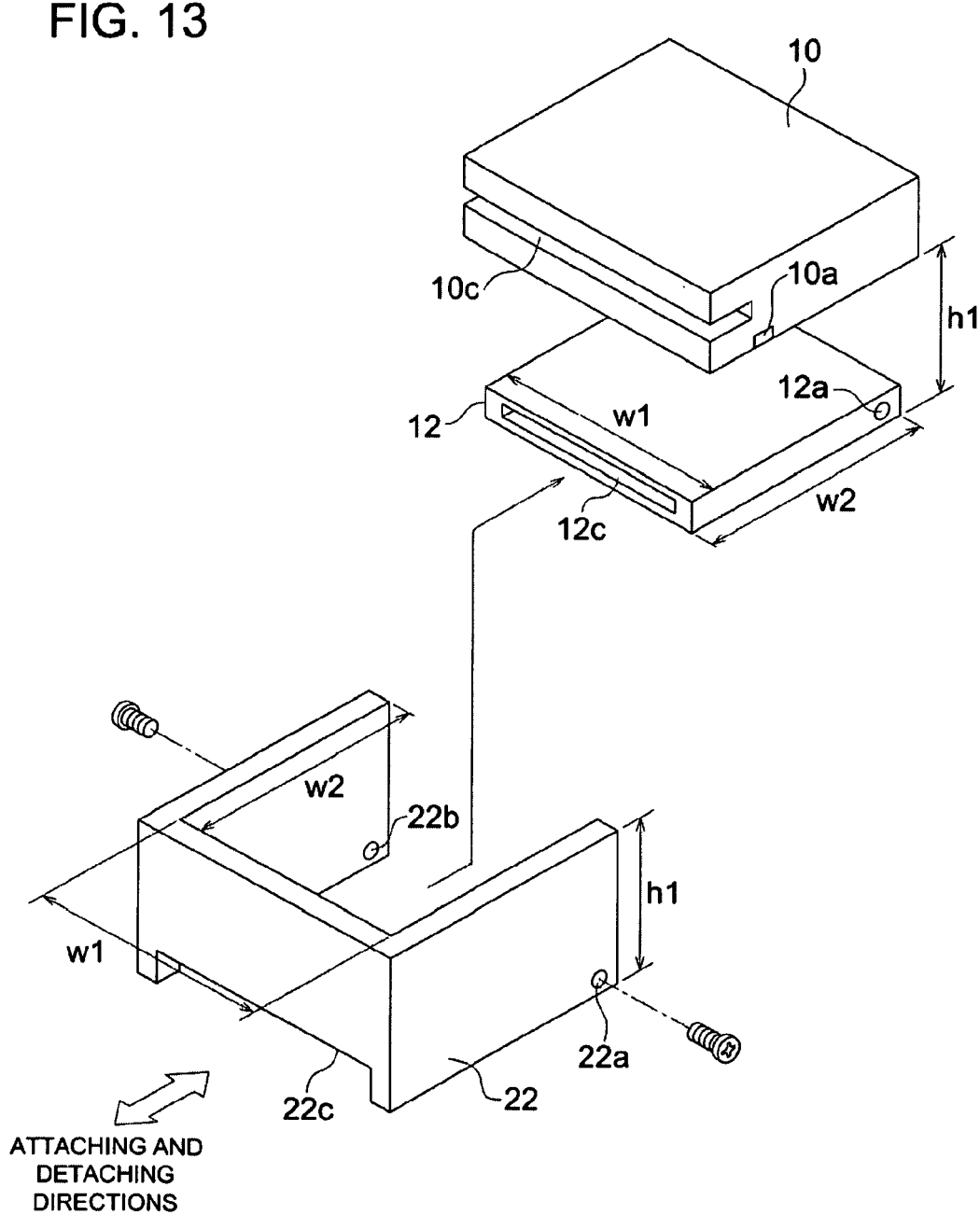
FIG. 13 is a diagram showing schematically subject table 10, detector holding section 12 and the first radiation shading member 22.

FIG. 13 is a diagram showing schematically subject table 10, detector holding section 12 and the first radiation shading member 22. As shown in FIG. 13, the first radiation shading member 22 is constituted to be capable of being mounted on detector holding section 12, and its height h1, width w1 and depth w2 are determined so that it covers a space between subject table 10 and detector holding section 12 in the case of setting the minimum enlargement factor (first radiographing enlargement factor: 1.46 times, here). This first radiation shading member 22 has screw holes 22a and 22b, and when screws are inserted respectively in screw holes 12a and 12b (unillustrated) after the screw holes 22a and 22b are aligned respectively with screw holes 12a and 12b, it is possible to fix it to the detector holding section 12. When the first radiation shading member 22 is mounted on the detector holding section 12, and when a relative distance between radiation source 6 and subject table 10 and a relative distance between the radiation image detector and subject table 10 are adjusted for radiographing at the minimum enlargement factor, the breast image radiographing apparatus 1 turns out to be in the state shown in FIG. 1.

Incidentally, the breast image radiographing apparatus 1 is one to conduct phase contrast radiographing, and the first radiation shading member 22 is constantly in the state to be mounted on the breast image radiographing apparatus 1, because the first radiation shading member 22 is required to be mounted at any enlargement factor. When conducting absorption contrast radiographing, the first radiation shading member 22 is removed so that the radiographing may be carried out.

Further, on the first radiation shading member 22, there is formed opening 22c at the position that corresponds to attaching and detaching slot 12c of detector holding section 12 when mounting on the detector holding section 12. Through this opening 22c, the radiation image detector can be attached or detached through attaching and detaching slot 12c of the detector holding section 12 under the condition where the first radiation shading member 22 is mounted.

Figure 14:
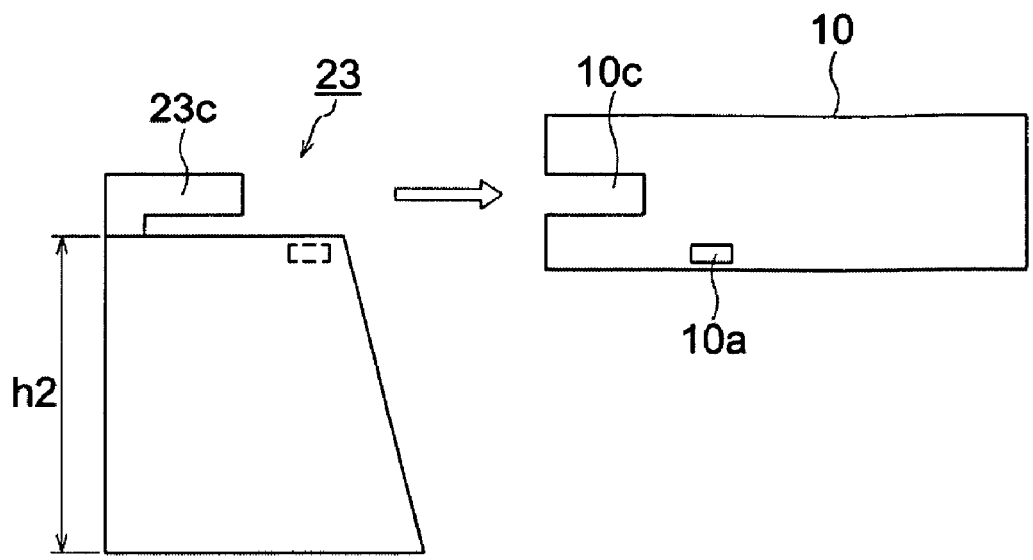
FIG. 14 (a) is a schematic diagram wherein the subject table 10 and the second radiation shading member 23 are viewed from the right side, and FIG. 14 (b) is a schematic diagram wherein the second radiation shading member 23 is viewed from the above.
Figure 14:
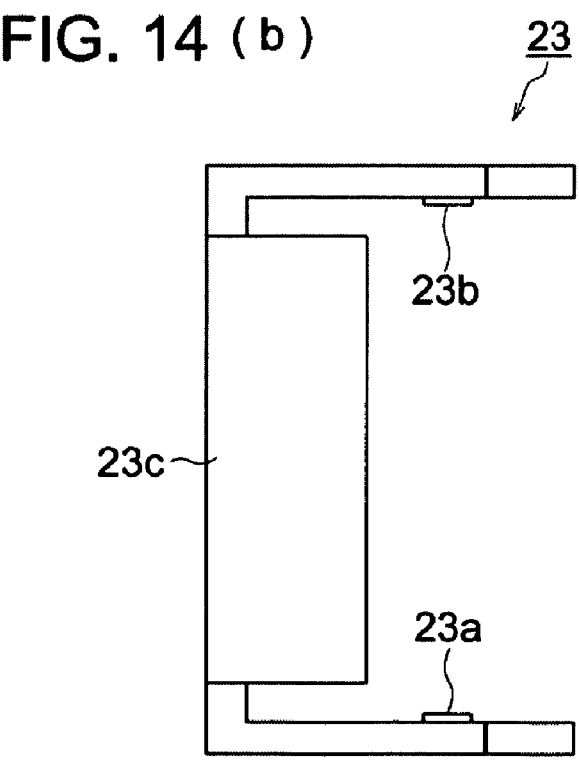
Figure 15:
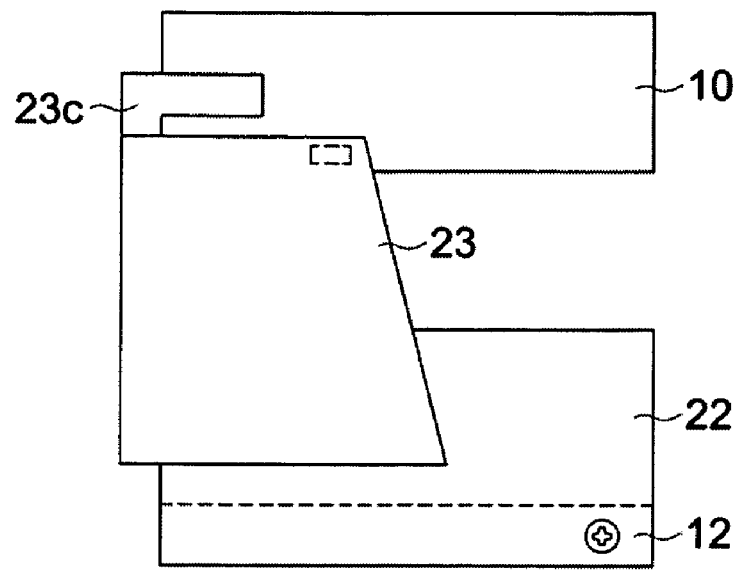
FIG. 15 (a) is a schematic diagram wherein the first radiation shading member 22 and the second radiation shading member 23 are mounted and are viewed from the right side, and FIG. 15 (b) is a schematic diagram wherein the first radiation shading member 22 and the second radiation shading member 23 are mounted and are viewed from the front side.
Figure 15:
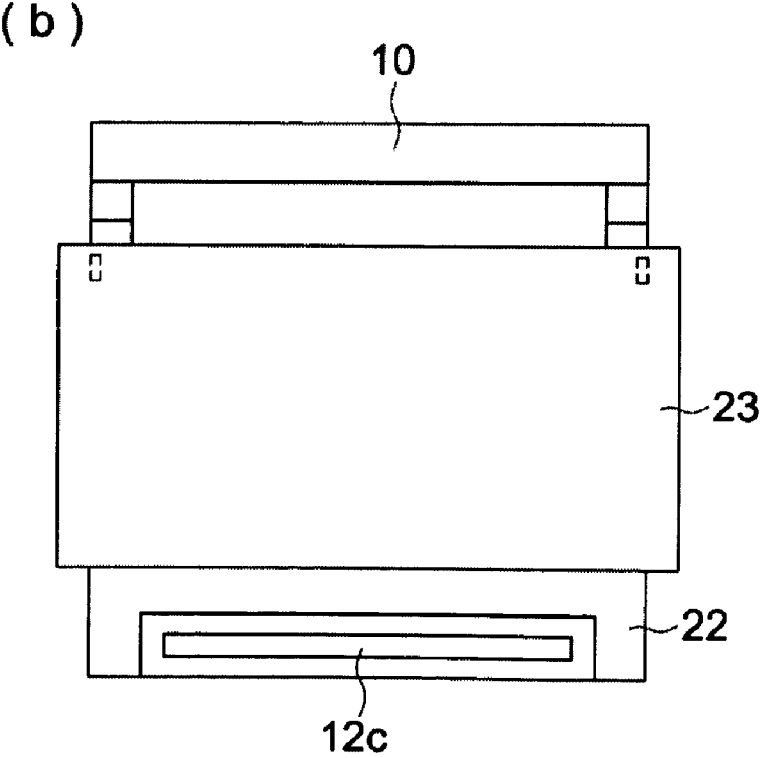

FIG. 14 (a) is a schematic diagram wherein the subject table 10 and the second radiation shading member 23 are viewed from a side, FIG. 14 (b) is a schematic diagram wherein the second radiation shading member 23 is viewed from the top side, FIG. 15 (a) is a schematic diagram wherein the first radiation shading member 22 and the second radiation shading member 23 are mounted and are viewed from a side, and FIG. 15 (b) is a schematic diagram wherein the first radiation shading member 22 and the second radiation shading member 23 are mounted and are viewed from the front side. The second radiation shading member 23 is one to be mounted on subject table 10, and as shown in FIGS. 14 (a) and 14 (b), engagement protrusion 23c having a hook-shaped sectional area that can be engaged with engagement recess 10c of subject table 10 is provided on the subject table 10, side end of it and magnets 23a and 23b each serving as a fixing member are provided at a position where the radiation shading member overlaps with subject table 10 when the radiation shading member is mounted on subject table 10. When the engagement protrusion 23c of the second radiation shading member 23 is engaged with engagement recess 10c of subject table 10, magnets 23a and 23b are attracted to magnetic material metal plates 10a and 10b of subject table 10. Thus, the second radiation shading member 23 can be fixed to subject table 10 by engagement of the engagement protrusion 23c with engagement recess 10c, attraction of magnet 23a to the magnetic material metal plates 10a and by attraction of magnet 23b to the magnetic material metal plates 10b.

The second radiation shading member 23 is one to cover a space when the space is formed undesirably between subject table 10 and the first radiation shading member 22 under the condition where the enlargement factor is set to an enlargement factor (second radiographing enlargement factor) which is greater than the minimum enlargement factor representing the first radiographing enlargement factor, and a distance between subject table 10 and detector holding section 12 is longer than that in the case of the minimum enlargement factor, and height h2 is determined so that a space between subject table 10 and the first radiation shading member 22 may be covered, according to the enlargement factor (according to enlargement factor 1.76 times or 2.63 times). When there are plural enlargement factors each being greater than the minimum enlargement factor and making radiographing possible, it is also possible to prepare the second radiation shading member 23 for each enlargement factor, or to prepare the second radiation shading member 23 having a height according to the maximum enlargement factor that makes radiographing possible. When a relative distance between subject table 10 to radiation source 6 and a relative distance between subject table 10 to detector holding section 12 are adjusted for radiographing at an enlargement factor greater than the minimum enlargement factor, and when the first radiation shading member 22 and the second radiation shading member 23 are mounted, the whole of breast image radiographing apparatus 1 results in the state shown in FIG. 12.

Even in the state where the first radiation shading member 22 and the second radiation shading member 23 are mounted, it is possible to attach or detach a radiation image detector through attaching and detaching slot 12c of detector holding section 12 through opening 22c, as shown in FIG. 15 (b).

In the phase contrast radiographing in the aforesaid structure, when an operator such as a radiographing technician mounts a radiation image detector on detector holding section 12 through opening 22c of the first radiation shading member 22, and when the operator conducts operations of a position adjustment switch of input device 14a and input the radiographing direction, driving device 17 is controlled by control device 16 depending on operations of the operator, and subject table 10 is adjusted to the position depending on a height of subject H and on the radiographing direction. If an enlargement factor is inputted from input device 14a by the operator and a position of compression board 11 is set after positioning of subject H, driving device 20 is controlled by control device 16, and holding member 8 is moved depending on the enlargement factor, whereby, a relative distance between subject table 10 and radiation source 6 and a relative distance between subject table 10 and a radiation image detector are adjusted, while, a relative distance between radiation source 6 and detector holding section 12 is kept to be constant. Then, the operator mounts the second radiation shading member 23 depending on the enlargement factor if the enlargement factor requires, and an instruction for radiographing is conducted by input device 14a. When mounting the second radiation shading member 23, the operator has only to cause engagement protrusion 23c of the second radiation shading member 23 to be engaged with engagement recess 10c of subject table 10. If radiographing is instructed, control device 16 conducts radiographing. In the course of radiographing, intrusion into a radiation irradiating area between subject table 10 and detector holding section 12 from the outside can be prevented by radiation shading member 22 and/or radiation shading member 23. Owing to this, it is possible to prevent a region other than patient's regions to be radiographed from being exposed and from being undesirable imaging in the image.

As described above, in the breast image radiographing apparatus 1, a radiation shading member is made to be the first radiation shading member that has opening 22c and is common to all enlargement factors and to be the second radiation shading member that can be attached or detached in response to the enlargement factor. Therefore, it is possible to attach to or detach from detector holding section 12 of the radiation image detector easily, while keeping the first radiation shading member 22 that is needed for all enlargement factors to be mounted on the breast image radiographing apparatus 1, thus, easiness for attaching and detaching of the radiation image detector in the case of using a radiation shading member can be improved.

The breast image radiographing apparatus 1 in each of the First-Fourth Embodiments has been described as described above, and contents of the description in the aforesaid each embodiment is a preferable example of the breast image radiographing apparatus 1 relating to the invention, and the invention is not limited to this. Further, detailed structures and detailed operations of the breast image radiographing apparatus 1 can be varied properly without departing from the spirit and scope of the invention.

The invention claimed is:

1. A radiographic imaging apparatus which conducts phase contrast radiographing, the radiographic imaging apparatus comprising:
a radiation source whose focus size D is 30 (μm) or more;
a detector holding device which holds a radiation image detector for detecting a radiation which emitted from the radiation source and which has been transmitted through a subject;
a subject table which is used for fixing the subject and which is arranged between the radiation source and the detector holding device, and can be mounted after selection from a plurality of different sizes;
a holding device for keeping a distance between the radiation source and the detector holding device to be constant;
an adjusting device which adjusts relative distances of the subject table to the radiation source and to the radiation image detector;
a subject table size information acquiring device which acquires size information about the subject table mounted;
a control device which controls the adjusting device based on the acquired subject table size information; and
wherein the radiographic imaging apparatus conducts the phase contrast radiographing under a condition of $R1 \geq (D-7)/200$ (m) when R1 represents a distance from the radiation source to the subject.

2. The radiographic imaging apparatus described in claim 1,
wherein a distance L (m) between the radiation source and the detector holding device is 0.95 (m) or more.

3. The radiographic imaging apparatus described in claim 2,
wherein the focus size D is 100 (μm).

4. The radiographic imaging apparatus described in claim 1,
wherein the control device causes the adjusting device to adjust the relative distances to distances wherein a radiation image of whole of the subject held on the subject table can be detected by the radiation image detector held by the detector holding device, based on the acquired subject table size information.

5. The radiographic imaging apparatus described in claim 1, the radiographic imaging apparatus further comprising:
a detector size acquiring device which acquires information of a size of the radiation image detector,
wherein the control device controls the adjusting device based on the acquired subject table size information and on the acquired size information of the radiation image detector.

6. The radiographic imaging apparatus described in claim 1, the radiographic imaging apparatus further comprising:
a setting device which sets a radiographing enlargement factor, wherein the control device judges whether the radiation image of the whole of the subject held on the subject table can be detected by the radiation image detector held by the detector holding device or not, when radiographing at the set radiographing enlargement factor based on the acquired subject table size information and on the set radiographing enlargement factor, and the control device controls the adjusting device based on a result of the judgment.

7. The radiographic imaging apparatus described in claim 6, further comprising:

a warning device which gives a warning, wherein the control device causes the warning device to give a warning when a part of a radiation image of the subject held on the subject table is judged to be unable to be detected by the radiation image detector when radiographing at the set radiographing enlargement factor, and the control device controls the adjusting device to adjust the relative distances based on the set radiographing enlargement factor, when a radiographing permission signal for radiographing at the set radiographing enlargement factor is inputted.

8. The radiographic imaging apparatus described in claim 6, wherein the control device judges whether the radiation image of the whole of the subject held on the subject table can be detected by the radiation image detector held on the detector holding device or not, when radiographing at the set radiographing enlargement factor, based on the acquired subject table size information and on the acquired size information of the radiation image detector.

9. The radiographic imaging apparatus described in claim 6, wherein when the radiation image of the whole of the subject can be detected according to the result of the judgment, the control device controls the adjusting device based on the set radiographing enlargement factor, and wherein when the radiation image of the whole of the subject cannot be detected according to the result of the judgment, the control device controls the adjusting device based on a maximum radiographing enlargement factor which enables the radiation image of the whole of the subject to be detected.

10. The radiographic imaging apparatus described in claim 1, wherein the detector holding device comprises:

an attaching-detaching slot through which the radiation image detector is attached and detached; and a radiation shading member which covers a space between the subject table and the detector holding device, wherein an opening through which the radiation image detector can pass is formed at a position of the radiation shading member corresponding to the attaching-detaching slot on the detector holding device.

11. The radiographic imaging apparatus described in claim 10, wherein the radiation shading member is composed of a first radiation shading member which covers a space between the subject table and the detector holding device when radiographing at a first radiographing enlargement factor, and is composed of a second radiation shading member which covers a space formed between the first radiation shading member and the subject table when radiographing at a second radiographing enlargement factor wherein a distance between the subject table and the detector holding device is relatively longer than when radiographing at the first radiographing enlargement factor, and the opening is formed on the first radiation shading member.

* * * * *